(12) United States Patent
Sultan et al.

(10) Patent No.: US 10,937,106 B2
(45) Date of Patent: Mar. 2, 2021

(54) SYSTEM AND METHOD FOR PROCESSING PAYMENT BUNDLES

(71) Applicant: Cognizant TriZetto Software Group, Inc., Englewood, CO (US)

(72) Inventors: Jay Sultan, Athens, GA (US); Howard Downs, Northfield, IL (US); Dale Hoerle, Naperville, IL (US)

(73) Assignee: Cognizant TriZetto Software Group, Inc., Englewood, CO (US)

( * ) Notice: Subject to any disclaimer, the term of this patent is extended or adjusted under 35 U.S.C. 154(b) by 246 days.

(21) Appl. No.: 16/299,264

(22) Filed: Mar. 12, 2019

(65) Prior Publication Data

US 2019/0213687 A1 Jul. 11, 2019

Related U.S. Application Data

(62) Division of application No. 14/277,037, filed on May 13, 2014, now Pat. No. 10,262,374, which is a division of application No. 13/110,182, filed on May 18, 2011, now Pat. No. 8,756,075.

(51) Int. Cl.
| | |
|---|---|
| *G06Q 40/08* | (2012.01) |
| *G06Q 50/22* | (2018.01) |
| *G06Q 20/00* | (2012.01) |
| *G06Q 10/10* | (2012.01) |
| *G16H 40/20* | (2018.01) |

(52) U.S. Cl.
CPC ............ *G06Q 40/08* (2013.01); *G06Q 10/10* (2013.01); *G06Q 20/00* (2013.01); *G06Q 50/22* (2013.01); *G16H 40/20* (2018.01)

(58) Field of Classification Search
CPC ........ G06Q 40/08; G06Q 10/10; G06Q 20/00; G06Q 50/22; G16H 40/20
USPC ....................................................... 705/4, 2–3
See application file for complete search history.

(56) References Cited

U.S. PATENT DOCUMENTS

| | | |
|---|---|---|
| 4,491,725 A | 1/1985 | Pritchard |
| 4,858,121 A | 8/1989 | Barber et al. |
| 4,916,611 A | 4/1990 | Doyle, Jr. et al. |

(Continued)

FOREIGN PATENT DOCUMENTS

| | | | |
|---|---|---|---|
| DE | 19641357 | 9/1998 | ............ G06F 17/60 |
| JP | 11242270 | 9/1999 | ............ G03B 15/05 |

(Continued)

OTHER PUBLICATIONS

Hussey, Peter S et al., "Episode-based performance measurement and payment: making it a reality.", Sep. 9, 2009, Health affairs (Project Hope) vol. 28,5 (2009): 1406-17. doi:10.1377/hlthaff.28. 5.1406 (Year: 2009).*

(Continued)

*Primary Examiner* — Joy Chng
(74) *Attorney, Agent, or Firm* — Dawn-Marie Bey; Bey & Cotropia PLLC

(57) ABSTRACT

A system and process for prospectively creating patient episodes of care and triggering associated payment bundles during the claim adjudication process facilitates real-time claim pricing in accordance with payment bundle rules to facilitate episodic payment in place of pay-for-service payment. Additionally, various processes are described for modeling patient episodes and payment bundles and unbundling episodic payments.

15 Claims, 7 Drawing Sheets

(56) References Cited

U.S. PATENT DOCUMENTS

| | | |
|---|---|---|
| 5,134,564 A | 7/1992 | Dunn et al. |
| 5,191,522 A | 3/1993 | Bosco et al. |
| 5,235,507 A | 8/1993 | Sackler et al. |
| 5,253,164 A | 10/1993 | Holloway et al. |
| 5,301,105 A | 4/1994 | Cummings, Jr. |
| 5,324,077 A | 6/1994 | Kessler et al. |
| 5,333,317 A | 7/1994 | Dann |
| 5,339,434 A | 8/1994 | Rusis |
| 5,359,509 A | 10/1994 | Little et al. |
| 5,410,675 A | 4/1995 | Shreve et al. |
| 5,471,382 A | 11/1995 | Tallman et al. |
| 5,493,671 A | 2/1996 | Pitt et al. |
| 5,517,405 A | 5/1996 | McAndrew et al. |
| 5,539,787 A | 7/1996 | Nakano et al. |
| 5,544,044 A | 8/1996 | Leatherman |
| 5,581,558 A | 12/1996 | Horney, II et al. |
| 5,583,760 A | 12/1996 | Klesse |
| 5,644,778 A | 7/1997 | Burks et al. |
| 5,692,501 A | 12/1997 | Minturn |
| 5,704,044 A | 12/1997 | Tarter et al. |
| 5,708,828 A | 1/1998 | Coleman |
| 5,724,379 A | 3/1998 | Perkins et al. |
| 5,793,771 A | 8/1998 | Darland et al. |
| 5,815,689 A | 9/1998 | Shaw et al. |
| 5,832,447 A | 11/1998 | Rieker et al. |
| 5,835,897 A * | 11/1998 | Dang ................ G06Q 10/087 705/2 |
| 5,845,254 A | 12/1998 | Lockwood et al. |
| 5,879,163 A | 3/1999 | Brown et al. |
| 5,890,129 A | 3/1999 | Spurgeon |
| 5,907,490 A | 5/1999 | Oliver |
| 5,915,241 A | 6/1999 | Giannini |
| 5,930,759 A | 7/1999 | Moore et al. |
| 5,950,168 A | 9/1999 | Simborg et al. |
| 5,950,169 A | 9/1999 | Borghesi et al. |
| 5,970,463 A | 10/1999 | Cave et al. |
| 5,991,733 A | 11/1999 | Aleia et al. |
| 5,991,876 A | 11/1999 | Johnson et al. |
| 6,012,035 A | 1/2000 | Freeman, Jr. et al. |
| 6,052,524 A | 4/2000 | Pauna |
| 6,088,677 A | 7/2000 | Spurgeon |
| 6,094,684 A | 7/2000 | Pallmann |
| 6,111,893 A | 8/2000 | Volftsun et al. |
| 6,112,183 A | 8/2000 | Swanson et al. |
| 6,208,973 B1 | 3/2001 | Boyer et al. |
| 6,226,658 B1 | 5/2001 | Smith |
| 6,253,186 B1 | 6/2001 | Pendleton, Jr. |
| 6,283,761 B1 | 9/2001 | Joao |
| 6,324,516 B1 | 11/2001 | Shults et al. |
| 6,341,265 B1 | 1/2002 | Provost et al. |
| 6,343,271 B1 | 1/2002 | Peterson et al. |
| 6,453,297 B1 | 9/2002 | Burks et al. |
| 6,529,876 B1 | 3/2003 | Dart et al. |
| 6,542,905 B1 | 4/2003 | Fogel et al. |
| 6,587,829 B1 | 7/2003 | Camarda et al. |
| 6,618,808 B1 | 9/2003 | Johnson et al. |
| 6,658,630 B1 | 12/2003 | Threatt et al. |
| 6,665,685 B1 | 12/2003 | Bialic |
| 6,735,569 B1 | 5/2004 | Wizig |
| 6,763,346 B1 | 7/2004 | Nishida et al. |
| 6,915,265 B1 | 7/2005 | Johnson |
| 7,016,856 B1 | 3/2006 | Wiggins |
| 7,194,416 B1 | 3/2007 | Provost et al. |
| 7,344,496 B2 | 3/2008 | Iliff |
| 7,346,522 B1 | 3/2008 | Baylor et al. |
| 7,389,245 B1 | 6/2008 | Ashford et al. |
| 7,464,040 B2 | 12/2008 | Joao |
| 7,774,252 B2 | 8/2010 | Seare et al. |
| 7,904,317 B1 * | 3/2011 | Lesswing ................ G06Q 40/00 705/4 |
| 8,489,415 B1 * | 7/2013 | Ringold ................ G06Q 10/10 705/2 |
| 2002/0019754 A1 | 2/2002 | Peterson et al. |
| 2002/0077869 A1 | 6/2002 | Doyle et al. |
| 2002/0138304 A1 | 9/2002 | Fontanesi |
| 2002/0178120 A1 | 11/2002 | Reid et al. |
| 2002/0194008 A1 | 12/2002 | Yang et al. |
| 2003/0023466 A1 | 1/2003 | Harper |
| 2003/0033162 A1 | 2/2003 | Houssiaux et al. |
| 2003/0033240 A1 | 2/2003 | Balson et al. |
| 2003/0046093 A1 | 3/2003 | Erickson et al. |
| 2003/0046116 A1 | 3/2003 | Horowitz et al. |
| 2003/0061174 A1 | 3/2003 | Menninger |
| 2003/0084004 A1 | 5/2003 | Morciniec et al. |
| 2003/0097329 A1 | 5/2003 | Nabe et al. |
| 2003/0115156 A1 | 6/2003 | Baker |
| 2003/0149594 A1 * | 8/2003 | Beazley ................ G06Q 10/10 705/2 |
| 2003/0212582 A1 | 11/2003 | Taschner |
| 2003/0216946 A1 * | 11/2003 | Ferraro ................ G06Q 40/02 705/4 |
| 2004/0024683 A1 | 2/2004 | Morciniec et al. |
| 2004/0034607 A1 | 2/2004 | Piccinelli |
| 2004/0083119 A1 | 4/2004 | Schunder et al. |
| 2004/0085355 A1 | 5/2004 | Harmes et al. |
| 2005/0033609 A1 | 2/2005 | Yang |
| 2005/0033612 A1 * | 2/2005 | Donovan ................ G06Q 40/08 705/4 |
| 2005/0091143 A1 | 4/2005 | Schmidt et al. |
| 2005/0108067 A1 | 5/2005 | Chapman et al. |
| 2005/0187797 A1 | 8/2005 | Johnson |
| 2005/0247777 A1 | 11/2005 | Pitroda |
| 2006/0085311 A1 | 4/2006 | Hoerle et al. |
| 2007/0203834 A1 | 8/2007 | Field |
| 2010/0235197 A1 | 9/2010 | Dang |
| 2011/0153371 A1 * | 6/2011 | Lesswing ................ G06Q 40/04 705/4 |
| 2012/0123798 A1 * | 5/2012 | Lanzalotti ................ G06Q 10/10 705/3 |
| 2012/0173273 A1 | 7/2012 | Asdhford |

FOREIGN PATENT DOCUMENTS

| | | | |
|---|---|---|---|
| WO | WO 84/01448 | 4/1984 | ............ G06F 3/00 |
| WO | WO 91/15817 | 10/1991 | ............ G06F 19/00 |
| WO | WO 95/03569 | 2/1995 | ............ G06Q 40/00 |
| WO | WO 95/12857 | 5/1995 | ............ G06Q 17/60 |
| WO | WO 99/22330 | 5/1999 | ............ G06F 19/00 |
| WO | WO 99/44111 | 9/1999 | ............ G06Q 20/00 |
| WO | WO 00/03343 | 1/2000 | ............ G06F 1/00 |
| WO | WO 00/66367 | 11/2000 | ............ B42D 1/10 |

OTHER PUBLICATIONS

United States Government Accountability Office, Private Sector Initiatives for Bundled Payments, Jan. 31, 2011, U.S. Government Accountability Office, pp. 1-17, https://www.gao.gov/new.items/d11126r.pdf (Year: 2011).*

U.S. Appl. No. 09/577,386, filed May 23, 2000, Lesswing, et al.

U.S. Appl. No. 10/923,539, filed Aug. 20, 2004, Hensley.

"National Health Plan Identifier, The Establishment of a Standard for a National Health Plan Identifier Issue Paper" [online], Mar. 11, 1998 [retrieved on Dec. 14, 2010], 13 pp., Retrieved from the Internet: http://www.payorid.com/Medicare/HIPAA.htm.

Kirby, William H., Jr., "Computer-Based Applications for Providers, Consumers and Insurers in Health Care Services and Education," *IEEE*, pp. 236-242, 1982.

North Carolina, Industrial Commission, Memorandum, "New Mandatory Medical Billing and Reimbursement Procedures," 2 pp., Nov. 30, 1999.

DownSeeker Scripts, "Free Download MedLink Script," 2 pp., Aug. 29, 1999.

The Free Library, "HNC Insurance Solutions Introduces AUTOADVISOR, the First Integrated Medical Repricing Software With Managed Care Component for the Auto Medical Claims Market" [online], *Business Wire*, Sep. 2, 1998 [retrieved on Dec. 14, 2010], 4 pp., Retrieved from the Internet: http://www.thefreelibrary.com/HNC+Insurance+Sol . . . .

Selby, Dayton W. and Federico, Robert J., "The Effects of Physicians' Computer Applications on Health Insurance Claims and Reimbursements," *IEEE*, pp. 746-751, 1979.

(56) References Cited

OTHER PUBLICATIONS

Miller, Lawrence G., "Reducing Health Care Costs Using Claims Adjudication Software" [online], *Physician Executive*, May 1, 1993 [retrieved on Dec. 14, 2010], 4 pp., Retrieved from the Internet: http://www.thefreelibrary.com/Reducing+health+ca . . . .

Waterhouse, Rosie, "Medical Tests for New Benefit 'Unfair': Over-Reliance on Health Evidence Attacked" [online], The Independent, Feb. 17, 1994 [retrieved on Dec. 20, 2010], 1 p., Retrieved from the Internet: http://www.independent.co.uk/news/uk/politics/medical-tests-for-new-benefit-unfair-overreliance-on-healt . . . .

Gustafson, Bobette M., "Preparing for Future Roles as Claims Payers" [online], *Healthcare Financial Management*, Jan. 1, 1996 [retrieved on Dec. 14, 2010[, 3 pp., Retrieved from the Internet: http://www.allbusiness.com/ . . ./538143-1.html.

"Repricing Window," The TriZetto Group, Inc., ClaimBatch Entry—CBE, Section 8—Adding Other Information, 12 pp.

Contract Management Solutions, "Company Overview" [online], Retrieved on Aug. 3, 2004, Retrieved From: http://www.cmsi.com/company, 1 p.

Contract Management Solutions, "Solutions Overview" [online], Retrieved on Aug. 3, 2004, Retrieved From: http://www.cmsi.com/solutions, 1 p.

Dicarta Enterprise Contract Management, "Products" [online], Retrieved on Aug. 3, 2004, Retrieved From: http://www.dicarta.com/html/products, 9 pp.

Contract Management Solutions, "Contract Manager" [online], Retrieved on Aug. 3, 2004, Retrieved From: http://www.cmsi.com/solutions/cm.htm, 3 pp.

Contract Management Solutions, "Deal Manager" [online], Retrieved on Aug. 3, 2004, Retrieved From: http://www.cmsi.com/solutions/dm.htm, 1 p.

Contract Management Solutions, "Technology" [online], Retrieved on Aug. 3, 2004, Retrieved From: http://www.cmsi.com/solutions/tech.htm, 1 p.

Dicarta Enterprise Contract Management, "Healthcare" [online], Retrieved on Aug. 3, 2004, Retrieved From: http://www.dicarta.com./html/products/healthcare.cfm, 2 pp.

Contract Management Solutions, "Compliance" [online], Retrieved on Aug. 3, 2004, Retrieved on Aug. 3, 2004, Retrieved From: http://www.cmsi.com/solutions/compliance.htm, 2 pp.

Contract Management Solutions, "CMXchange" [online], Retrieved on Aug. 3, 2004, Retrieved From: http://www.cmsi.com/solutions/cmxc.htm, 1 p.

International Search Report & Written Opinion issued for PCT/US2005/036971 dated Dec. 26, 2006.

Press Release, "TriZetto Introduces NetworX Modeler" [online], Nov. 18, 2003 [retrieved on Apr. 18, 2011], 2 pp., Retrieved From the Internet: http://www.trizetto.com/newsEvents/pressReleases/2003-11-18_NetworXModeler.asp.

IBM, Solutions for Healthcare Management, "TriZetto NetworX and IBM: Driving Costs Out of Healthcare Management," 2 pp., Copyright 2009.

The Gantry Group, "ROI Value Delivery Through Streamlined Provider Contract Modeling" [online], [Retrieved on Apr. 18, 2011], 1 p., Retrieved From the Internet: http://www.gantrygroup.com/healthcare/research/detail.cfm?product_id=561.

"Healthcare Solutions: Health Plans—NetworX Pricer" [online], Copyright 2000-2011 [retrieved on Apr. 18, 2011], 1 p., Retrieved From the Internet: http://www.trizetto.com/hpSolutions/networXPricer.asp.

EHealthPartners, "TriZetto NetworX Pricer™ & Modeler™" [online], [Retrieved on Apr. 18, 2011], 1 p., Retrieved From the Internet: http://www.ehealthpartners.com/Applications/ApplicationExpertise/TriZettoNetworXPrice . . . .

White Paper, "The Gantry Group: Is TriZetto® NetworX Modeler® Delivering on its ROI Promise?," Copyright 2010, 8 pp.

"Preferred Care Partners Selects TriZett's Facets Software and Specialized Components to . . . ", *Business Wire*, May 26, 2005, 2 pp.

"CareSource Selects TriZetto's CareAdvance Enterprise Software and Specialized Components to Help It Administer Medicaid Business" [online], *Business Wire*, 2 pp., Sep. 5, 2006 [retrieved on Apr. 18, 2011], Retrieved From the Internet: http://www.medinfonews.com/ar/1r.htm.

"CareFirst BlueCross BlueShield Selects TriZetto's NetworX Pricer Software to Automate Claims Pricing and Help Manage Costs" [online], Sep. 21, 2006 [retrieved on Apr. 18, 2011], 1 pp., Retrieve From the Internet: http://goliath.ecnext.com/coms2/gi_0199-5783145/CareFirst-BlueCross-BlueShield-Select . . . .

"Blue Shield of California Launches Work on System-Wide Technology Upgrade With TriZetto's Facets Software" [online], Jan. 29, 2008 [retrieved on Apr. 18, 2011], 1 pp., Retrieved From the Internet: https://www.blueshieldca.com/bsc/newsroom/pr/LegacyModernization_012908.jhtml.

"Blue Cross and Blue Shield of Minnesota Will Use TriZetto's NetworX Suite to Move Toward Value-Based Reimbursement Models" [online], *Business Wire*, May 11, 2010 [retrieved on Apr. 18, 2011], 2 pp., Retrieved From the Internet: http://www.businesswire.com/news/home/20100511005321/en/Blue-Cross-Blue-Shield-M . . . .

"Patient-Centered Primary Care Collaborative, Commonwealth Fund, Dartmouth Institute Release Landmark Consensus Document on ACOs, Medical Homes" [online], Apr. 12, 2011 [retrieved on Jun. 7, 2011], EMR and Health IT News, 9 pp., Retrieved From the Internet: http://www.emrandhipaa.com/news/2011/04/12/patient-centered-primary-care-collaborative-commonwealth-fund-dartmouth-institute-release-landmark-consensus-document-on-acos-medical-homes.

Feucht, Daniel Francis, et al., "Session # 46 PD: ICD-10: Implications on Pricing, Reserving, IT and Strategy," Society of Actuaries, SOA '10 Health Meeting, Jun. 28-30, 2010, 27 pp.

"ICD-10-CM-PCS MS-DRG Conversion Project, ICD-9-CM Coordination & Maintenance Committee," Centers for Medicare & Medicaid Services, Sep. 16, 2009, 74 pp.

International Search Report and Written Opinion for PCT Application No. PCT/US2007/070298, dated Jan. 7, 2008, pp. 1-11.

* cited by examiner

| Bundle | MS-DRG | Average Medicare Cost (2007) | Bundle Source |
|---|---|---|---|
| Heart Bypass or Valve - Major | 216, 219, 231, 233, 235 | $37,254 | CMS |
| Heart Bypass or Valve - Minor | 217, 220, 232, 234, 236, 218, 221 | $24,545 | CMS |
| Insertion of Heart Defibrillator | 226, 227 | $25,461 | CMS |
| Insert Stent in Heart | 246, 248, 250, 247, 249, 251 | $10,453 | CMS |
| Pacemaker | 242, 258, 260, 243, 261, 244, 259, 262 | $11,612 | CMS |
| Hip Replacement | 461, 466, 469, 488, 467, 462, 468, 470, 489 | $9,288 | CMS |
| Knee Replacement | same | $9,288 | IHA |

FIGURE 4
(PRIOR ART)

SYSTEM AND METHOD FOR PROCESSING PAYMENT BUNDLES

CROSS-REFERENCE TO RELATED APPLICATIONS

The present application is a division of U.S. patent application Ser. No. 14/277,037, filed May 13, 2014, entitled "System and Method For Processing Payment Bundles," which is a division of U.S. patent application Ser. No. 13/110,182, filed May 18, 2011, entitled "System and Method For Processing Payment Bundles," now U.S. Pat. No. 8,756,075, the disclosures of which are incorporated herein by reference in their entireties.

FIELD OF THE INVENTION

The embodiments described herein are generally directed to system and methods for creating payment bundles. More particularly, the embodiments are directed to prospectively creating patient episodes of care and triggering associated payment bundles, during the claim adjudication process and repricing claims in accordance with the payment bundle to facilitate episodic payment in place of pay-for-service payment.

BACKGROUND OF THE INVENTION

In an effort to contain or reduce the rate at which health care costs are increasing in the United States, employers, at-risk commercial insurers, and the government increasingly are pursuing a new approach to provider reimbursement—one that emphasizes value—instead of volume. Value-based reimbursement (VBR) is a category of reimbursement methods that reward physicians and other providers for taking a broader, more active role in the management of member health and pays them for results instead of solely for visits or procedures.

Many forms of VBR involve shifting clinical and financial risk from payers to providers when providers are better-positioned to manage that risk. In particular, payment bundling and/or episode-of-care payments, some forms of accountable care organizations and some versions of the patient-centered medical home take focused approaches to placing the right degree of risk with provider organizations.

Payment bundling is the circumstance wherein Payers are provided the ability to pay a payment bundle rate to a single provider for an episode of care. A payment bundle rate is defined as a pricing method in which a flat amount covers a defined group of procedures and services that fall within the episode of care. To that end, Payers need a solution to process payment bundles (also known as global case rates). A payment bundle is defined as multiple providers joining together contractually to accept a single payment for an entire episode of care. Ideally, the individual providers still perform the same services and submit separate claims as they do today, but Payers need a way to process the individual claims in accordance with the requirements of the payment bundle. An example of what might be included in a single payment bundle might be, payment for inpatient stay, the surgeon, anesthesiologist, rehabilitation facility, primary care physician, ER, and other providers required to deliver the care related to a hip replacement. The payment bundling serves as a payment guideline for multiple providers and services reimbursing a single provider for the entire case and pricing to zero all of the other provider claims. It is then the provider groups' responsibility to reimburse all members appropriately.

Payment bundling stimulates collaboration among providers, aligning their financial interests and increasing care coordination. Such collaboration can result in improved utilization, reductions in complications and other forms of unwarranted variations in care and resulting negative outcomes, while care coordination can help reduce lengths of stay and improve hand-offs among providers.

Accordingly, Payers and/or purchasers need a way to transform the claims stream currently used for fee-for-service (FFS) health care payments into a single (or possibly multiple) episodic payments. It is preferred that such transformation occur before any payments are made (prospectively), rather than as a reconciliation process after payments are made (retrospectively). However, FFS claims are not designed to support episodic payment and current software systems cannot transform FFS claims into episodic payments at the time of adjudication. Current systems and processes pay out all claims in a bundle at 100% and then must go back and retrospectively or post-adjudication.

SUMMARY OF THE INVENTION

In accordance with a first embodiment, a process for repricing individual provider claims is described. The process includes: receiving, at a processing system, from a payer a first data set including first specific data from a first individual provider claim; analyzing, by the processing system, the first data set to determine one of the following: (a) the first individual provider claim is part of an existing payment bundle; (b) the first individual provider claim triggers creation of a patient event and an associated payment bundle; (c) the first individual provider claim is neither (a) or (b); and (d) the first individual provider claim should be held up to a predetermined amount of time pending receipt by the processing system of additional data or passage of the predetermined amount of time. The process further includes transmitting to the payer, by the processing system, at least one of the following responses in accordance with the analysis: (e) the first individual provider claim is not part of an existing or associated payment bundle, pay the provider under non-payment bundle terms; (f) the first individual provider claim is part of an existing or associated payment bundle, pay the provider under one of existing or associated payment bundle terms; and (g) the first individual provider claim did not contain enough information, delay payment to the provider.

In a second embodiment a process for creating a patient event, triggering a payment bundle associated with the created patient event and repricing individual provider claims in accordance with the payment bundle is described. The process includes: receiving, at a processing system, at least one of a data set including specific data from an individual provider claim and non-claim information; analyzing, by the processing system, the data set, non-claim information or the combination of the data set and non-claim information to determine if a patient event should be created and trigger an associated payment bundle; creating, by the processing system, a patient event and triggering the associated payment bundle, wherein the patient event has an associated patient identification (ID) and a preliminary date range; searching, by the processing system, at least a first database of the processing system to identify any previously received individual provider claims that are included in the associated payment bundle, wherein the search compares a patient ID for each previously received individual provider claim to the associated patient ID and compares a date for each previously received individual provider claim to the preliminary date range; repricing, by the processing system, an amount that should have been paid to a provider of each identified previously received individual provider claim that matches associated patient ID and occurred within preliminary date range in accordance with pre-established rules defining the associated payment bundle; and reporting, by the processing system, the repriced amount that should have been paid to providers of each identified previously received individual provider claims in the associated payment bundle.

In a third embodiment a process for modeling payment bundles is described. The process includes: importing, into at least a first database, historical data for multiple types of claims; receiving, by a processor, a selection of at least one representative claim for payment bundle modeling; modifying, by the processor, the data associated with the selected at least one representative claim to reflect a specific date range; reviewing, by the processer, the modified data associated with the selected at least one representative claim to identify at least one event therein to use to trigger a payment bundle; searching, by the processor, the at least a first database, to identify claims related to the modified representative claim, wherein a claim is related if it falls in the specific date range and meets one or more additional predetermined criteria; associating, by the processor, the modified representative claim and identified related claims with the at least one event used to trigger a payment bundle; and determining, by the processor, a modeled price for the payment bundle, the modified representative claim and any identified related claims.

BRIEF DESCRIPTION OF THE FIGURES

The following figures are intended to exemplify embodiments described herein and are considered part of the disclosure.

FIG. 4 illustrates exemplary prior art bundles;

DETAILED DESCRIPTION

Figure 1:
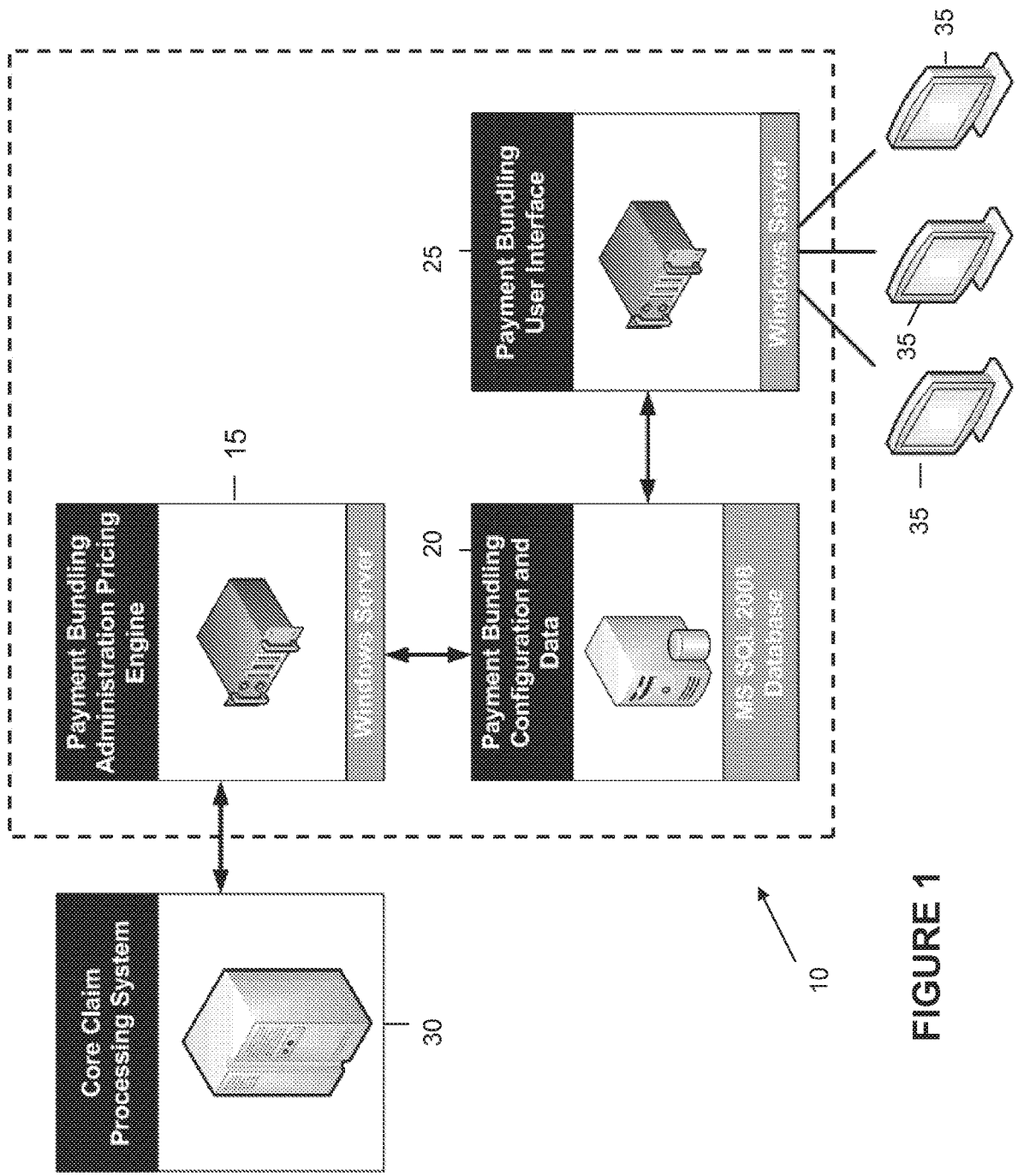
FIG. 1 illustrates and exemplary system configuration of the present embodiments for implementing the processes described herein.

The following terms and definitions are provided to assist the reader and provide context and examples. One skilled in the art recognizes that the definitions provided herein may not necessarily be inclusive of all possible alternatives. Likewise, other terms and phrases may be used in the art but have the same definitions provided herein.

ACO: A legal entity comprised of an eligible group of participants that work together to manage and coordinate care for Medicare fee-for-service (FFS) beneficiaries. These organizations are primary care-focused and must establish a mechanism for shared governance that provides all ACO participants with an appropriate proportionate control over the ACO's decision-making process as well as the opportunity to earn payments for "shared savings" if it meets quality performance standards established by the HHS Secretary.

Administrative Provider: The designated Provider responsible for receiving, unbundling and distributing single episode payments to individual Providers contracted to participate in a Patient Episode. Examples could include hospitals, ACOS, third-party administrators, any designated distributor.

CCPS: Core Claims Processing System. Any system used by a Payer to receive and process, i.e., adjudicate, claims from Providers Payer: Generally refers to entities other than the patient that finances or reimburse the cost of health services. In most cases, this term refers to insurance carriers, other third-party payers, or health plan sponsors (employers or unions). Payers can be a government, e.g., Canada, and are often referred to as "single payer" systems.

Payment bundle: A payment bundle defines a global case rate for a specific provider group which might consist of multiple individual providers, e.g., a facility, surgeon, anesthesiologist, etc. It defines the payment bundle pricing amount, the services to be included, categorization of these services, date parameters and the definition of when a patient event should be created thus triggering when claims are to be processed or reprocessed in accordance with the Payment bundle.

Patient event or episode: A patient event or episode (used interchangeably) defines that a specific patient is participating in a specific payment bundle at a specific point in time. It specifies at least the claimant, the payment bundle being performed, date attributes (e.g., admission, discharge and procedure) and the date window for potential claims.

Patient bundle: The patient bundle is the claims that have been included in the created patient event. Elements include at least the patient event ID, claim number, payment bundle pricing and categorization of the claim.

Provider: any person or entity furnishing any healthcare service or item for which any person or governmental or private third-party payer makes a payment. This includes without limitation any person or entity who is a provider or supplier under the Medicare program. And any person or entity who receives any payment from any patient, governmental, health care program or private third payer for the provision of any health care service or item. May also include any person or entity who submits claims on behalf of any of the above. Specific provider examples may include hospitals, clinics, laboratories, health care professional (physicians, mid-level providers, nurse practitioners; rehabilitation facilities; imaging centers, durable medical equipment (DME) providers, or groups of health care professionals (e.g., ACO).

Referring to FIG. 1, a Payment Bundling Administration System (PBAS) 10 in accordance with the embodiments described herein includes at least a pricing engine 15 (e.g., Microsoft Windows Server), a database for payment bundling data and configurations storage 20 (e.g., Microsoft SQL), and user interface application 25 (e.g., Microsoft Windows Server). One skilled in the art recognizes that multiple servers and/or processors and databases may be used to implement the processes described herein. The PBAS 10 communicates with a core claim processing system (hereafter "CCPS") 30. The CCPS could be any one of numerous types of systems and services for processing and adjudicating health related claims such as The TriZetto Group's FACETS or QNXT products. The PBAS is accessible through at least a web-based interface by multiple users 35.

In a particular exemplary configuration, the pricing engine 15 may be a monolithic server application using a Web-service based real-time interface for claims and other communication with the CCPS. The user interface may be a browser-based thin client, using, for example, Model View Presenter architecture. The PBAS supports batch and Web-services for non-claim events, such as pre-notifications and pre-authorizations discussed further below. The PBAS 10 supports a clustered server environment for processing, where multiple servers would be able to access a single database. There are numerous implementation-specific ways to load into such an environment using .NET as a load balancer or a third-party load balancer.

A necessary precursor to payment bundling processing is a contracting process whereby individual providers who provide individual services within a patient episode agree to forego fee-for-service payment from the payer and instead agree to receive distributed payment after the payer makes an episodic payment to an administrative provider. This contract can take on various forms. For example, a hospital that has a payment contract with a payer could negotiate specific payment bundling payment contracts with the payer and agree to receive a single bundled payment from the payer for one or more services provided by the hospital that are part of a patient episode. As one skilled in the healthcare art understands, numerous individual providers, e.g., doctors, laboratories, rehabilitation centers, may provide individual services at the hospital as part of a patient episode. These doctors would likely have their own contracts with the payer, separate and apart from the hospital's contract, and they could also have a contract with the hospital that includes provisions relating to payment bundling. While a hospital is a good example of an administrative provider, other entities could serve in this capacity as well, e.g., ACO. For example, an entity could be formed to act solely as the administrative provider on behalf of member providers—the entity does not itself need to be a provider of health-related services. Exemplary systems and methods for facilitating contract modeling and negotiation are described in co-pending U.S. patent application Ser. No. 10/923,539 entitled System and Method for Modeling Terms of a Contract under Negotiation to Determine their Impact on a Contracting Party which is incorporated herein by reference in its entirety.

Figure 2B:
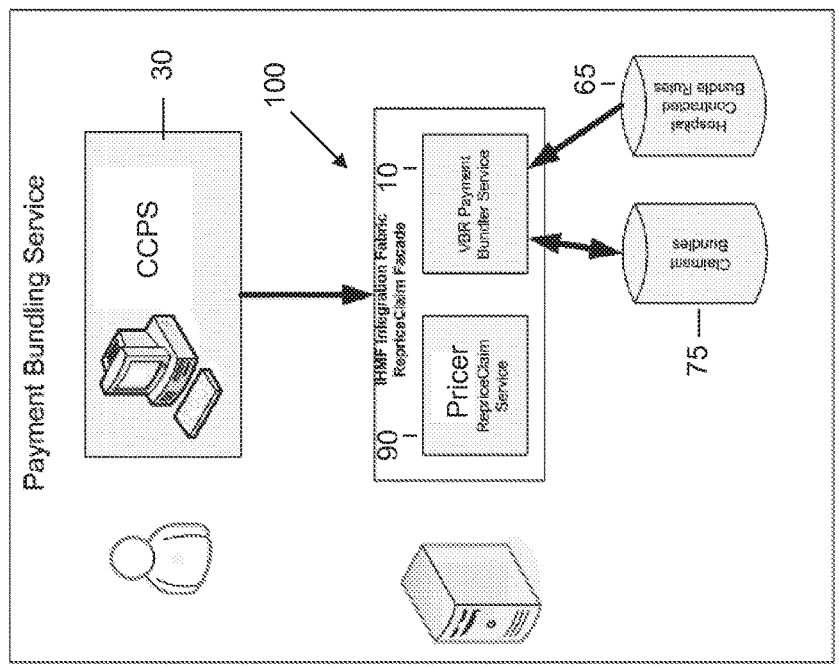
FIGS. 2a and 2b illustrate exemplary process flows and system components for implementing payment administration and payment bundling services as described herein.
Figure 2A:
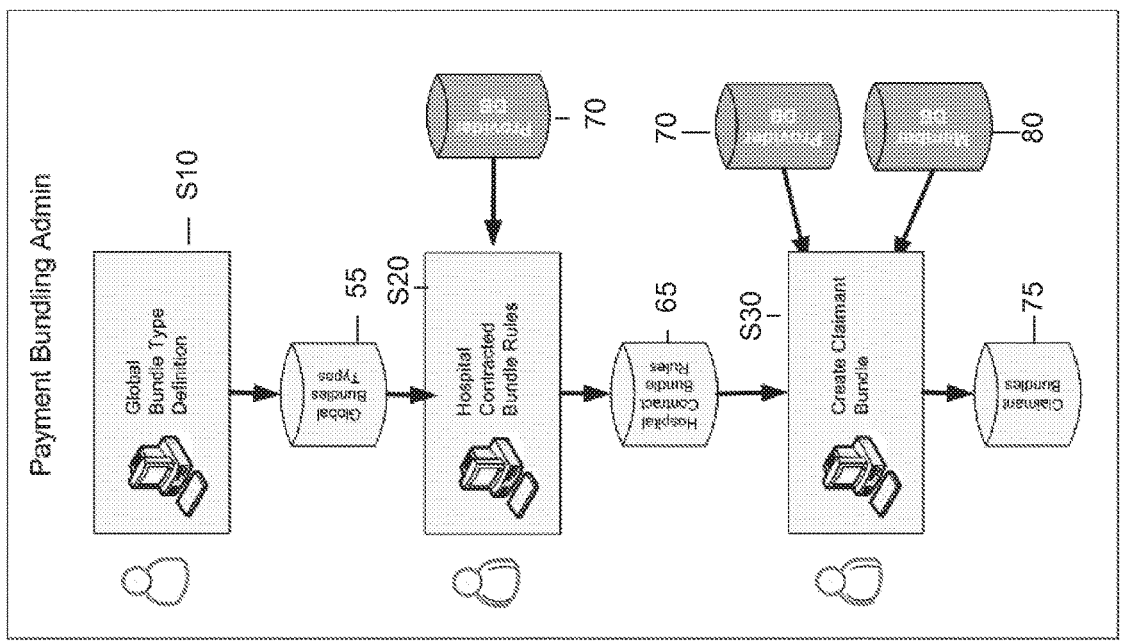

Referring to FIG. 2*a*, the payment bundling administration process generally includes defining global bundle types S10 to identify at least pricing amount, the services to be included, categorization of those services, date parameters and the definition of when a patient event should be created. Categorization allows for calculating subtotal costs or utilization into categories that allow for retrospective analysis. For example, what is the total amount paid out for surgery costs (inclusive of all claims from all surgeons) or how many rehabilitation visits did the patient receive or how much was spent post-discharge (adding up figures from numerous providers). Comparing such figures across multiple bundles assist in the improvement of the care delivery. Step S10 populates a database of defined bundles types 55. Next, there are bundle-specific contract rules established S20 in order to determine, among other things: how an episode is to be identified; what constitutes the creation of a specific episode for a specific patient's care; how specific individual services are determined to be part of an episode; and what business process can be used to evaluate any specific fee-for-service claim to determine if it belongs to an episode or if it is not impacted by episodic logic. Step S20 populates a database of contract bundle rules 65 using data from, e.g., administrative providers (hospital etc.) and from individual providers (depicted as provider database 70). Finally, the bundle types and corresponding contract rules are used to populate a database of claimant (payment) bundles 75 using data from, e.g., administrative providers (hospital etc.) and individual providers (depicted as provider database 70) as well as members (patients) (depicted as member database 80).

While FIG. 2*a* refers generally to a representative high level schematic for payment bundling administration, FIG. 2*b* is a representative high level schematic for the payment bundling service aspect of the present embodiments. More specifically, during the service aspect, an administrator at the CCPS 30 sends a web service call to the PBAS 10 including specific claim information. The PBAS 10 utilizes claimant bundle data from database 85 and contract rules from database 65 to ascertain the price of the submitted claim. As depicted, the PBAS 10 is accessible as part of a larger pricing engine system 100 which can also include a separate, adjudication pricing service 90.

Figure 3:
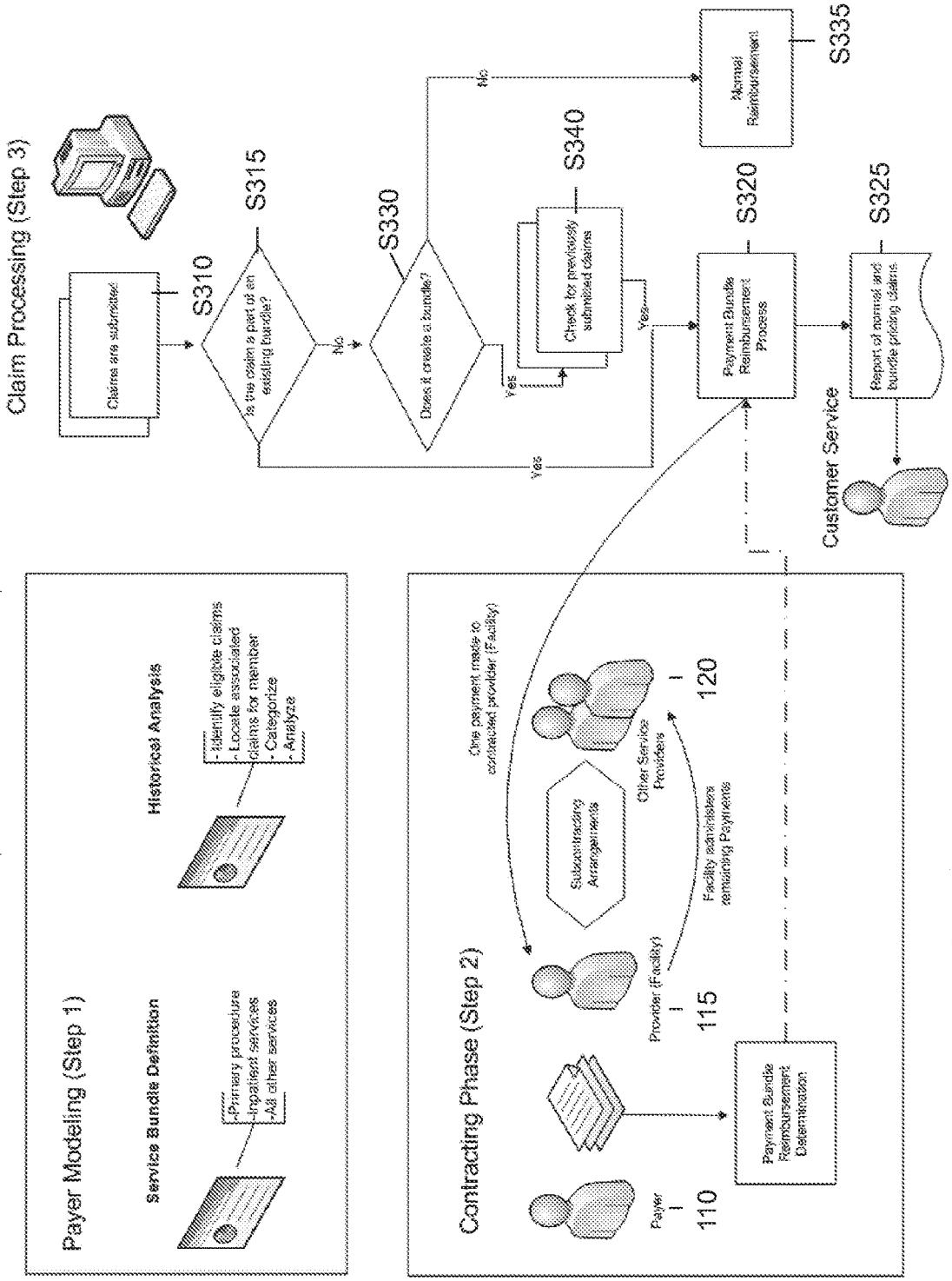
FIG. 3 illustrates exemplary process flows and participants for various phases of an overall process for implementing payment bundling.

Referring to FIG. 3, a more particular example of a payment bundling process, including administration and service aspects, is illustrated. Step 1, modeling, refers to the data types, collection and analysis undertaken by either a bundle modeling feature of the PBAS (or stand-alone application) to identify the types of claims/services that should or could be part of a bundle and to establish an initial price and other details for the modeled bundle. The Step 1 modeling process can be undertaken separate and apart from Steps 2 and 3 as described further herein in detail. Further, the modeling process may be offered as a stand-alone application or service, separate and apart from the PBAS. As part of this modeling, the modeling application could start with pre-configured, global bundle definitions that have previously been established and include, as appropriate, for each bundle: primary procedure(s), inpatient service and other services. For example, FIG. 4 is a chart showing exemplary bundles as defined by Centers for Medicare & Medicaid Services (CMS) and Integrated Healthcare Associate (IHA). CMS identifies the procedures by their diagnosis related group codes (MS-DRG) and provides an average cost. There is no requirement that the bundle be modeled after the CMS or IHA, but such bundles provide a starting point for defining the major service aspects for inclusion in a bundle for common, high volume procedures. Alternatively, the modeler could model bundles from scratch using available, historical claim data and analysis. In most instances, there is a wealth of pre-existing historical data from which to model bundles. The historical analysis includes, e.g., identification of potentially eligible claims, location of claims associated with the identified eligible claim, categorization and analysis.

More specifically, a stand-alone application or companion application offered as part of the PBAS is a Payment Bundling Modeling (PBM) application that applies payment bundling logic to historical claims data. This allows the determination of how care delivered in the past would have been bundle and priced if it had been paid under payment bundling rules. The product will allow for comparisons of the total pricing under historical methods of claim pricing (e.g., fee-for-service) and the same claims paid under payment bundling scenarios, as well as variations in the terms used to do payment bundling, so different sets of payment bundling rules can be compared based on how the historical claims would be affected. Additionally, this product has functionality for prospectively estimate total cost in the future based on historical cost; for generating return-on-investment (ROI) projections based on historical data; and for selecting among different combinations of providers that might be eventually recruited into the group of providers accepting the bundle. This PBM application would have the ability to, among other things, import claims data from CCPSs or receive manually; filter imported data according to, for example, data range and/or Group; purge claims that have been previously imported based on date range; and combine claims from multiple sources. The PBM application could also identify candidate administrative providers in a list of candidate administrative providers listed by provider ID and has the ability to select a list of candidate administrative providers from a result set created by a query-by-example window. Further still, the PBM application has the ability to select payment bundle definitions for modeling for a specific candidate administrative provider. The PBM application can create variants of the payment bundle definitions by changing attributes or business logic for the variants and to modify dates and amounts of the baseline data. The PBM application can model the modification of utilization within a patient event; limit the claims to be processed using, e.g., a query-by-example window; process claims against modeling sets; create patients events for each candidate administrative provider for each payment bundle definition and include claims for each patient event; and modify the dates and allowed amount data on the historical claims for the purpose of creating output that can be more easily compared to other alternatives. Another set of capabilities includes the ability to alter the utilization rates (such as the decrease in the price of a certain claim, the reduction in the number of claims—i.e., reduction in rehabilitation, or the occurrence rate of readmissions or infections), and project the resulting cost and utilization impact of such changes in utilization rates, utilization changes resulting from the adoption of payment bundling and the care collaboration it creates. Finally, the PBM application can manage the modeling characteristics and processes listed above, export the modeling data, compare versions of a single patient bundle within a modeling set and generate standard and ad hoc reports.

Figure 5:
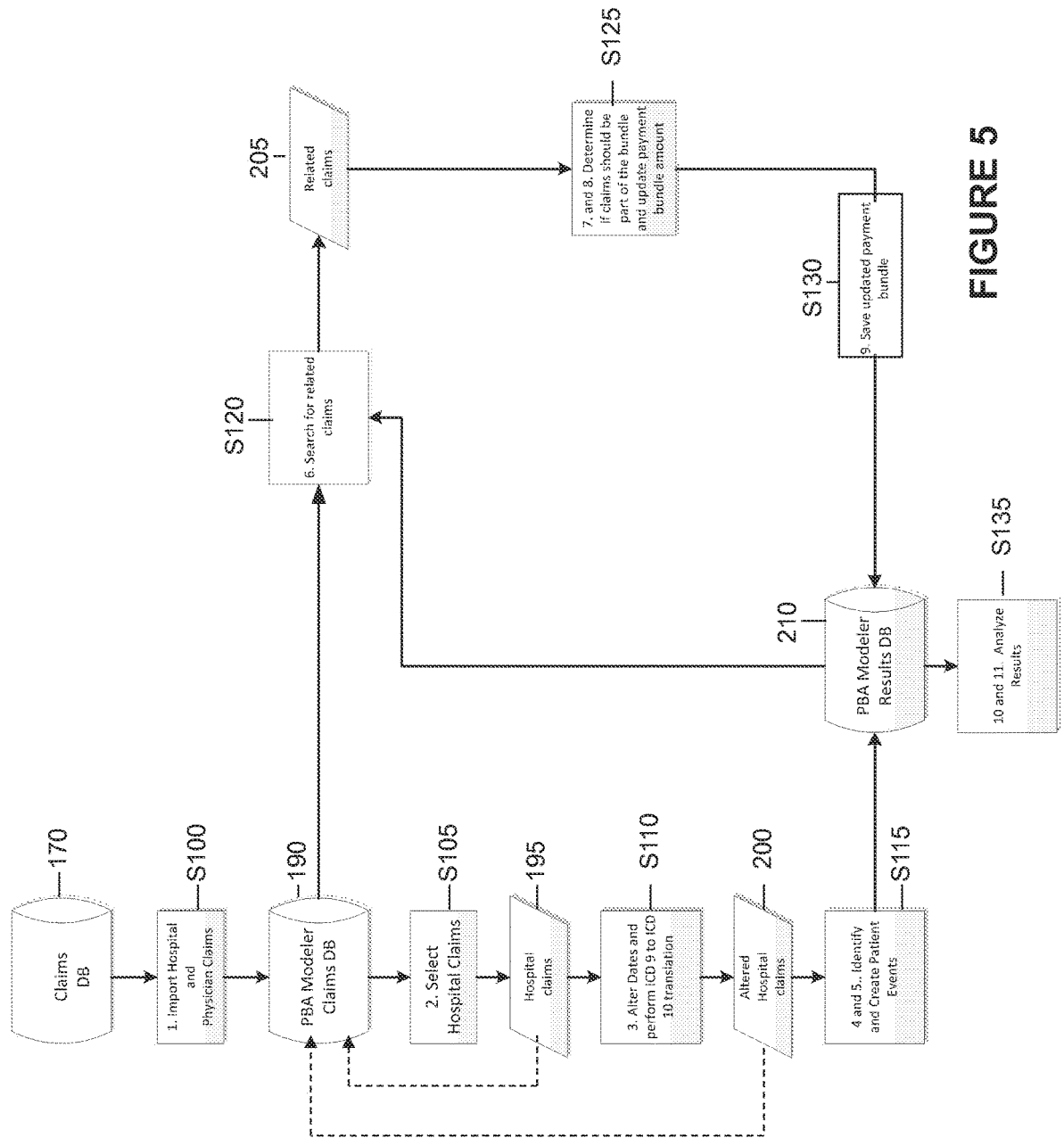
FIG. 5 illustrates an exemplary process flow for modeling payment bundles as described herein.
Figure 6:
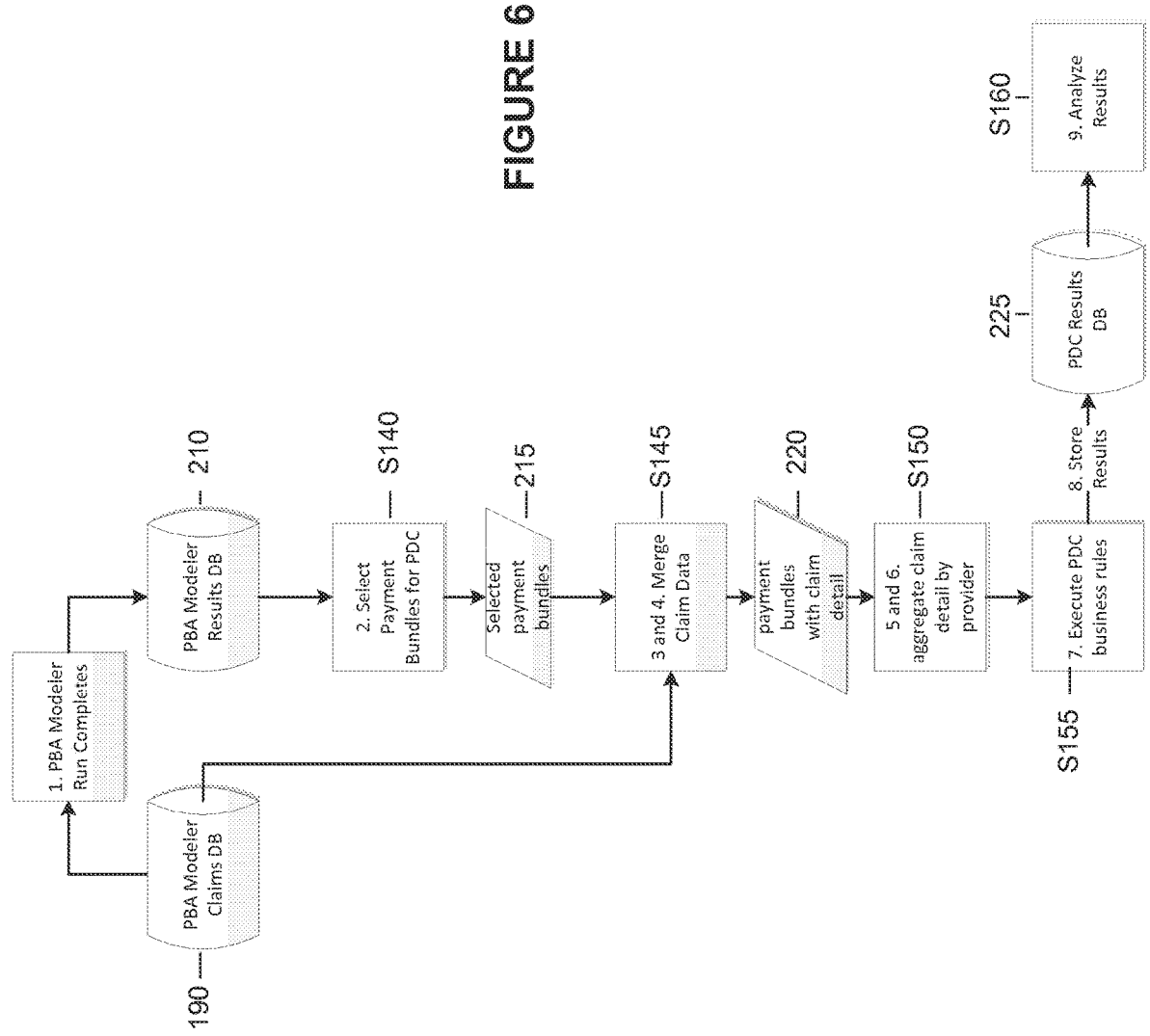
FIG. 6 illustrates an exemplary process flow for calculating individual provider payment in accordance with payment bundles as described herein.

A detailed description of various exemplary payment bundling modeling and pricing flows in accordance with the present embodiments are described herein with respect to FIGS. 5 and 6. Referring to FIG. 5, a payment bundle modeler flow includes the following steps. The PBM application includes logic that is run against data on a PBM system that includes at least a processor and database. One skilled in the art recognizes the many system components and configurations that may be implemented to meet the processor and storage requirements of the processes described herein. Initially, the PBM system imports claims data S100 from one or more historical claim databases 170 into one or more modeler claims databases 190. The historical claim information could be imported from various provider (e.g., hospital, ACO, physician) and payer databases or it could be entered manually through a user interface. Next, representative claims 195 are selected for modeling S105. This selection could be made based on numerous criteria, e.g., type of procedure, provider specialty, provider name, patient condition, location of primary procedure, etc. The selected claims 195 for modeling are saved in the modeler claims database 190. Next, the selected claim data is modified as necessary to return an accurate bundle model in view of, e.g., expected date range or event window around a primary procedure, regulations (e.g., ICD 9 to ICD 10) and the like S110. The modified selected claims 200 are saved in modeler claims database 190 and searched for patient events that could trigger a payment bundle S115. Identified triggering patient events are stored in modeler claims database 190.

Using information, e.g., patient ID, event window, from the selected 195 and modified claims 200, the PBM system searches the modeler claims database 190 for related claims 205, S120 and determines if the related claims 205 should be part of a patient event S125. Typically the event window would be set to a number of days (e.g., 30 days) prior to admission and a number of days (e.g., 60) post discharge. The PBM system saves all claims under the single patient event in the modeler results database 210 and adjusts the payment bundle details and projected single payment allowed amount in accordance therewith S130. Specific capabilities include the ability to alter the utilization rates (such as the decrease in the price of a certain claim, the reduction in the number of claims—i.e., reduction in rehabilitation, or the occurrence rate of readmissions or infections), and project the resulting cost and utilization impact of such changes in utilization rates, utilization changes resulting from the adoption of payment bundling and the care collaboration it creates. The PBM system also saves in one or more modeler results databases 210 the individual claim allowed amounts, i.e., fee-for-service amounts, for each of the individual claims that have been modeled as part of a patient event and associated payment bundle. Additionally, information about excluded claims is also retained.

Next, the PBM system facilitates viewing and analysis of modeled payment bundle results by comparing original fee for service allowed amount to new payment bundled allowed amount S135. As part of the analysis, the PBM system can prepare standard deviation analysis to identify outliers that will help the payer understand risk factors; prepare a distribution analysis across the provider population so the payer can determine how many procedures were performed by each provider and what percentage of the total procedures were done by any given provider; and summarize results into an ROI (return-on-investment) model that can be analyzed by the provider group and/or payer.

An additional feature of the PBM application is the ability to model electronic agreements between would-be participating providers for payment bundling disbursement. In other words, given a modeled payment model, how is the allowed payment distributed to the individual providers. The PBM application includes business rules for identifying the provider by role (e.g., surgeon, anesthesiologist, rehabilitation) or other criteria. There are separate rules for each role or type of provider, i.e., separate rules for surgeon, anesthesiologist, rehab, and hospital. The business rules may define a variety of circumstances that vary the individual provider payment amounts, including but not limited to, original fee-for-service amount, complications, or secondary diagnoses. The individual provider payment amounts may be calculated using logic that can be based on patient encounter data, such as length of stay, charge amount, total bundle amount, and original fee-for-service amounts.

For example, calculations could compare the payment bundle amount to the sum of all the original fee-for-service amounts for all claims submitted. If the payment bundle amount is larger than the original amounts, then each provider gets the original amount plus a share of the surplus. The following particular example is illustrative. For a payment bundle provider group consisting of a surgeon, an anesthesiologist and a hospital (also the administrative provider) the surgeon may receive 10% of the surplus up to 2 times the normal reimbursement, the anesthesiologist might receive 5% up to 1.5 times the normal reimbursement, with the remaining accruing to the hospital.

In a second example, if the payment bundle amount is less than the original amounts, then each provider gets the original amount minus a share of the deficit. By way of particular example, using the provider group consisting of a surgeon, an anesthesiologist and a hospital (also the administrative provider), the deficit could reduce the surgeon payment amount by 15% with a guaranteed reimbursement (minimum) of 90%. The hospital would absorb any remaining deficit.

Still another exemplary payout calculation could specify payment amount for a particular provider as a prorated amount of the bundle payment. This calculation may specify a percentage of the total bundled payment or it could simply be a fixed amount. Still further, individual provider business rules could specify other circumstances where the payment would be calculated differently. For example, the payment could be calculated as (a fixed amount+ a dollar amount)× (length of stay).

As the PBM system databases import information from various provider and payer databases, they become populated not only with more and more historical claims data, but with varying exemplary provider payout rules that can be used to model bundles and contracts. Such information could be useful for many purposes, including prospective formation of provider groups.

Accordingly, to this point, the PBM application has modeled the payment bundle and modeled the agreements between providers in a provider group(s) for administering the patient episode associated with a payment bundle and for unbundling, i.e., how final allowed payment bundle payout is distributed to individual providers. The PBM application further provides a payment disbursement calculator (PDC) that calculates the amount of the payment bundle amount to be paid out to each participating provider. As described above with respect to FIG. 5, the PBM produces the base modeled payment bundle data. Referring to FIG. 6, the PDC executes after payment bundles have been created. The PDC searches for and identifies relevant payment bundles S140, 215 that were created using the process in FIG. 5 and saved in modeler results database 210. When a bundle is identified, the PDC will retrieve data from the payment bundle, including payment bundle amount, associated claim IDs, and other necessary data which may be retrieved from provider systems, such as a Computerized Physician Order Entry system or a Clinical Decision Support System. The PDC will also retrieve the actual claims from the historical claim modeler database S145, 190 and produce payment bundles with claim detail according to provider 220. The PDC aggregates select claim detail data for each provider that participated in the encounter, including original charge amounts and allowed amounts for each claim and provider S150. The PDC executes pre-established business rules in the agreement to determine the payment amount for each provider S155. The PDC stores the calculated individual provider payment amounts, old fee for service amounts and other statistical claim data as needed for upcoming analysis in PDC results database 225.

The PDC can perform various analyses S160 including comparing a given provider's calculated amount to the amount she would have received under fee for service pricing. The PDC can also report on outliers and risk factors that help the providers understand which payment bundles fell out of the form and for what reason. The PDC may do comparison reporting to other similar providers. The provider may be able to get information that shows how many procedures she performed as compared to other providers in the area. The report could also do a reimbursement comparison. The PDC can be used in the modeling process or in the actual payment bundling scenario to unbundle payments for disbursement to individual providers. As discussed further herein, the PDC, which could also be provided as a separate, stand-alone module or as part of the larger PBM suite if modules, can perform unbundling of the payment bundle. By way of example, the PDC rules could pay out both based on utilization (e.g., a provider did 3 of something so they get paid 3× some price out of the bundle payment) and on performance (an action of the provider saved the hospital a lot of cost and a portion is paid back to the provider), as well as any savings remaining after all bundle "costs" have been paid out of the bundle payment.

Further to FIG. 3, Step 2 is a contracting step, wherein a payer 110 establishes a prime contract with an administrative provider 115 wherein the payer 110 agrees to pay the administrative provider 115 a single payment, i.e., payment bundle reimbursement determination (as shown), for a bundle of services. The administrative provider 115 has subcontracts with individual service providers 120 who perform various individual services within the bundle. The administrative provider 115 receives the single payment upon the appropriate claim trigger in accordance with the prime contract and dispenses subpayments to individual service providers 120 in accordance with the subcontracts. The PBM contract modeling functionality described herein may be used to establish prime or subcontracts referenced in FIG. 3, Step 2.

Further still, FIG. 3 illustrates Step 3 which is a high level process flow for claim repricing in accordance with embodiments described herein. By way of example, payer submits individual claims to the PBAS S310 as part of the adjudication process of claims received by the payor from a provider (including administrative provider). The PBAS engine determines if the submitted claim is part of an existing bundle S315. If the PBAS determines "yes" the claim is part of an existing bundle, the PBAS addresses in accordance with the payment bundle reimbursement process, e.g., most claims go to $0 with the exception of the bundle payment claim which triggers full payment of bundle amount S320. The appropriate amount is reported to the payor S325. If the PBAS determines "no" the claim is not part of an existing bundle, the PBAS next determines if the claim creates a bundle S330. If the PBAS determines "no" the claim does not create a bundle, the PBAS reports to the payor that the claim should be treated as a normal reimbursement, e.g., usually fee-for-service, S335. If the PBAS determines "yes" the claim does create a bundle, the PBAS checks the CCPS database for previously submitted claims that should have been treated as being part of the bundle S340, addresses in accordance with the payment bundle reimbursement process S320, and reports to the payor S325.

Particular examples and details regarding implementation of the processes described above are set forth below.

Initially, as discussed, an administrative provider is the link between the payer and the individual service providers and generally acts as the administrator of the payment bundle. In one exemplary scenario, the payer's CCPS assigns and stores provider identification information (provider IDs) for the administrative provider and, to the extent available, for each of the individual providers associated with the administrative provider and the payment bundling contract. In other situations only the PBAS knows the identity of the administrative provider and associated providers. As will be discussed later, the CCPS cannot possibly maintain perfect information regarding which individual providers are associated with which payment bundle at all times, but even incomplete listings are useful. Provider ID on a claim received at the CCPS helps the PBAS determine if a particular provider is on the list for a particular payment bundle. Further, a Provider ID could be the very information that triggers creation of a bundle (discussed below). Further still, even if the Provider ID is not enough information to trigger creation of payment bundle, the present embodiments can use this partial information, along with other information to determine that the claim is part of a payment bundle. Other information might include member/patient ID, timing, procedure, etc. Accordingly, the system and processes described herein account for situations wherein an administrative provider has numerous locums or moonlighting individual providers, e.g., short term doctors, such that updating the CCPS with provider IDs is not happening fast enough. The system allows for the identification of claims in bundle without the need for an individual provider ID to necessarily be linked to a particular payment bundle. In such an example, it is determined that any provider delivering services under a given situation (such as during an inpatient stay) is implicitly included in the bundle, without identification of the provider IDs.

Again, because there are numerous providers that can be involved, and these same non-administrative providers are often involved in multiple payment bundle definitions, it is very useful to create reusable lists of provider IDs. To that end, the present embodiments provide for the ability to have a list of provider function types that are used across the PBAS to categorize provider ID lists. The provider function type allows a generic reference in business logic that can be tied to specific lists for an administrative provider. Obviously an administrative provider can have zero to many lists of provider IDs associated with each administrative provider each of which is assigned a provider function type. The present embodiment provides for the ability to validate the individual provider IDs. Further, the PBAS can perform validation across different CCPS (with varying provider ID designations). Validation entails determining if it makes sense to use a particular provided in payment bundling. For most systems this mean that the provider ID exists and is not marked as inactive. Other validation features include: ability to validate at the time the provider ID is added to a list; ability to re-validate provider IDs; validation available on a user scheduled basis and/or through a user command; providing a list of invalid provider IDs; ability to use lists of provider IDs in business rules; ability to use provider lists in business rules for claims categorization; ability to test if the provider ID on a claim is in or not in the provider list and the ability to reference any of the provider lists that are defined for the administrative provider through the provider function type.

Set forth below are specific examples of contracting arrangements in accordance with the embodiments described herein. These examples are in no way intended to be limited, but instead are intended to be exemplary of the numerous variations that fall within the scope of the embodiments.

In a first example, ABC Hospital, which is an existing provider in the CCPS, contracts to be the administrative provider for a payment bundle. The payer administrator creates an administrator provider record that is tied to the provider in the CCPS by ABC Hospital's assigned Administrative Provider ID. The contract details are created in the PBAS and the contract is associated to ABC Hospital as the administrative provider. At a later time, if ABC Hospital agrees to a second payment bundle contract that bundles different areas of care, the second payment bundle contract is created in the PBAS and associated with the same Administrative Provider ID for ABC Hospital.

In a second example, a hospital system that operates three hospitals signs a single contract to do payment bundling with the payer. In this example, the hospital system would be the administrative provider for all payment bundles involving any one or more of the three hospitals.

In a third example, a payer creates a payment bundle, e.g., colonoscopy payment bundle, and enters into a contract with a specific physician, e.g., gastrointestinal physician, to be the administrative provider for the colonoscopy payment bundle.

In a fourth example, a payer operates its commercial business in a first CCPS and its Medicaid business in a second CCPS. ABC Hospital is setup as a provider in both the first CCPS and the second CCPS (but has different Provider IDs in each). The payer creates a single contract with ABC Hospital to do payment bundle for both commercial and Medicaid business, recognizing the separate Provider IDs point to the same entity, ABC Hospital, for adjudication and payment bundle processing.

In a fifth example, a payer has a group of anesthesiologists that has agreed to provide services as a part of the payment bundle. A payer administrator enters a list of Provider IDs for each of the individual anesthesiologists that can be used to determine that anesthesia claims including one of the listed Provider IDs are correctly included in a payment bundle.

The association of a particular administrative provider (through Provider ID) to a payment bundle is date driven. Note the following example: initially, an administrative provider associates ABC Hospital to a hip replacement payment bundle effective Jan. 1, 2011. The administrative provider knows that a new hip replacement payment bundle (e.g., new in that some attribute of the payment bundle will change) will take affect for ABC Hospital on Jul. 1, 2011. The administrative provider edits the existing administrative provider association to expire on Jun. 30, 2011 and creates a new association to the new payment bundle effective Jul. 1, 2011.

The payment bundle details come from multiple sources, including the CCPS and payer administrators through, e.g., the payment bundling user interface 25 of FIG. 1. The payment bundle defines one or more patient events for triggering the payment bundle. As described above with respect to payment bundling administration (see FIG. 2*a* and FIG. 3), payment bundle rules are defined and included as part of the business logic at the PBAS to determine when a particular claim triggers and/or should be included in a patient bundle for a particular payment bundle.

At the highest level, Patient identification (Patient ID) and Date Range in a claim provide a starting point for claim evaluation with respect to creation of patient events and payment bundle determinations. This is applicable during payment bundling administration (see FIG. 2*a*), payment bundling processing (see FIG. 2*b*), and payment bundle modeling (see FIG. 5). The following examples are instructive. In a first example, a payer administrator knows that all claims that might be added to the patient bundle for a particular payment bundle would occur within a range of dates 10 days prior to patient admission and 20 days after the discharge. By supplying these values around the admit/discharge date range, the PBAS can ignore all claims for this Patient ID outside of this date range. In a second example, a payer administrator is setting up a bundle for a procedure that includes certain types of services within 5 days of the procedure and other services within 30 days of the procedure. By supplying a date range of 0 days before the procedure and 30 days after the procedure, the processing engine can ignore all claims outside this date range.

In addition to Patient ID and Date Range, the following claim attributes may be used as part of the business rules that are applied by the PBAS to incoming claims to determine if a claim is to be included as a part of payment bundle: Patient gender; Patient Age (derived) and based on this calculation will derive the Patient DOB; Product ID; Clinical Service attributes including Admission date, Admission source, Admission type, Discharge date, Discharge status. Procedure code, Modifier (claim line level), Additional Modifiers (claim line level), Procedure date, Procedure type, DRG code, APC code, ASC code, APG code, Diagnosis Code, Diagnosis Code for ICD 9, Diagnosis Code for ICD 10, Service from date, Service to date, Units, Units of service, Place of service, Service Type, Length of Stay; Provider attributes including Provider type, Provider related facility, Provider specialty; Claim submission attributes including Claim type, Allowed charges, Total charges, and Original considered charge.

The following examples illustrate how various attributes may be used to define the payment bundle and instruct the PBAS to determine claim inclusion. In a first example, a payer administrator knows that claims by any anesthesiologist for a specific list of diagnosis codes within a patient bundle date range should be included in the payment bundle. The payer administrator creates business rules using these variables against the known diagnosis codes and specialty type. In a second example, a payer administrator knows that any office visits (a list of CPT codes) for a patient between the ages of 11 years and 70 years that occur within a patient bundle date range should be included in the patient bundle. The payer administrator creates business rules using these variables against the known procedure codes and patient age. In a third example, a payer administrator knows that all claims submitted by a list of 90 Provider IDs that have total charges less than $10,000 and have been discounted should be included in the payment bundle. The payer administrator creates business rules using these variables against the known provider list, total charge amount and allowed charge amount. Finally, in a fourth example, a payer administrator knows that a claim including a particular Medicare ambulatory payment classification (APC) code is not only included in the patient bundle but it is the claim used to pay the patient bundle. A payer administrator creates a business rule using this variable against the known APC code.

The PBAS has the ability to recognize multiple similar payment bundle definitions, based on an attribute of the payer's member (e.g., patient). This is important since the payment bundle particulars may vary by member designation. An initial evaluation by the PBAS based on member attribute could be based on for example, Employer, Group, Sub-group, Class, Plan and/or Product. Since much of the payment bundle definition will be the same across all members, the rules for inclusion of claims and rules to determine patient events can be reused across multiple similar bundles, thus simplifying the process of defining payment bundles for the payer administrator. But the PBAS still allows for distinct values in a specific bundle as compared to other bundles. Distinct values may include information such as: the member attributes listed above; the total amount paid for the bundle; the inclusion of some services in the bundle, such as rehabilitation; and the providers involved in the bundle. The following examples are illustrative.

In a first example, a payer administrator knows that there are two versions of a hip replacement bundle, one for most of the members and one specific for an employer (e.g., Group=IBM). While both groups have the same rules to determine when a payment bundle exists and to determine the basic services include in the bundle, the payment bundle definition for IBM as an employer has a higher bundle amount and different rules for the inclusion of rehabilitation than the others. The payer administrator sets up the different payment bundle definitions, reusing much of what was in the first one when creating the second.

In a second example, a payer administrator knows that a given payment bundle would only apply to patients in three groups. The payer administrator sets the initial processing for the payment bundle to only include these groups. Authorizations for a member in one of the three groups are evaluated against the business rules of patient event creation for the three groups.

In a third example, a payer administrator knows that when a patient is being treated by a specific physician with a specific procedure code, a patient event occurs. The payer administrator further knows that there is no specific groups/class/plan excluded from this specific payment bundle. The payer admin sets the initial processing flag for this payment bundle to false, which suppresses the execution of payment bundle-specific business rules for this payment bundle. The payer administrator instead creates a business rule that defines a patient event based upon the specific procedure code and physician ID.

In a fourth example, a payer administrator knows that a patient event can be triggered either by a claim with a specific combination of diagnosis code and procedure code or by a specific DRG from a specific hospital for any patient in a list of three plans. The payer admin sets the initial processing flag for this payment bundle to false and creates two business rules, one for diagnosis plus procedure and one for DRG plus provider ID for the hospital, either of which can create a patient event. If both occur, only one patient event is created.

In a fifth example, a payer administrator knows that a given payment bundle would only apply to patients in one group. The payer administrator sets the initial processing for the payment bundle to only include the one group. Members in other groups do not have any further business rules evaluated for this payment bundle. Members in the relevant group are processed against the business rules of patient event creation as set for the relevant group.

Additionally, the present embodiments provide for the ability to define services that are specifically not included in the payment bundle. By way of example, a payer administrator knows that moving a patient from an inpatient stay to a long-term care hospital requires that hospitalist (provider specialty) charges should be excluded from the patient bundle. A payer administrator creates a business rule using these variables against the known discharge code for long-term care hospital. The sequence of the rule evaluation order allows this type of rule to assist the development of the payment bundling logic. For example, the first rule processed can exclude a claim for surgery due to trauma. The subsequent rule processed can include any surgical claim. In combination, this allows for all surgical claims to be included except for surgical claims due to trauma.

The PBAS business logic allows for evaluation of multiple logical terms using nested logic. For example, a payer administrator knows that a claim with a length of stay fewer than 5 days and a specific type of procedure (which can be expressed through a CPT code, a Revenue code, or a ICD9-CM code, all of which are different codes) should be included in the patient bundle. A payer administrator creates a business rule using the length of stay variable and requiring that one of the CPT/Revenue/ICD9-CM codes match a known value for each.

The present embodiments accept rules defining a payment bundle price as a flat fee or as a percent of charges. A flat fee is a set price, paid one time to the administrative provider. An example of the percentage of charge pricing is as follows: a payer administrator knows that a specific payment bundle should be paid at 225% of what the hospital typically receives for the hospital stay central to a payment bundle. The payer administrator provides business rules to identify the claim that is central to the payment bundle and sets the 225% value to be calculated against the allowed amount for the hospital's claim.

Additionally, the present embodiments allow for the ability to define allowed amount of included claims, i.e., not the claim that triggers payment to administrative provider. These allowed amounts are usually zero ($0) and "no paid," but could also be some other set amount (e.g., a payer administrator knows that a wheelchair claim from a durable medical equipment provider that is included in the payment bundle should be paid a flat $200, regardless of the billed amount) or a percentage of charges (e.g., a payer administrator knows that all rehab claims (a specific provider type) that are included in the payment bundle should be paid at 75% of charges or all care related to a surgical site infection is part of the bundle but only paid at 50% of charges.).

Once the various payment bundling contracts have been formed and the core business rules defined as described above, the PBAS is ready to process claims for inclusion in a patient bundle. As various examples and aspects of the processing process are described herein, additional rules, definitions, actions will be identified. Importantly, all providers still generate fee-for-service or encounter data claims as normal and these claims are submitted, directly or indirectly, to a payer. For example, a hospital will generate a claim for the facility cost using traditional revenue codes or DRG codes. Separately, the surgeon still generates a series of claims for evaluating the patient, doing the surgery, and then doing follow-up care on the patient. These claims are submitted to the CCPS for adjudication. At one of before, during, or post-adjudication, the CCPS sends claim information (described below) to the PBAS for processing in accordance with payment bundling logic. Importantly, the present embodiments do not require any additional or different coding and the providers do not have to change their current fee-for-service work process. As a caveat, there could be certain changes made to the fee-for-service claims to facilitate episodic payment, but these are all valid and typical for fee-for-service claim processing. For example, a provider today might leave the Place of Service field blank in their claims, but episodic payment may work better if Place of Service field is properly coded. This change in process is not altering the process of submitting fee-for-service claims, but meeting the same requirements in a different, valid manner.

Figure 7:
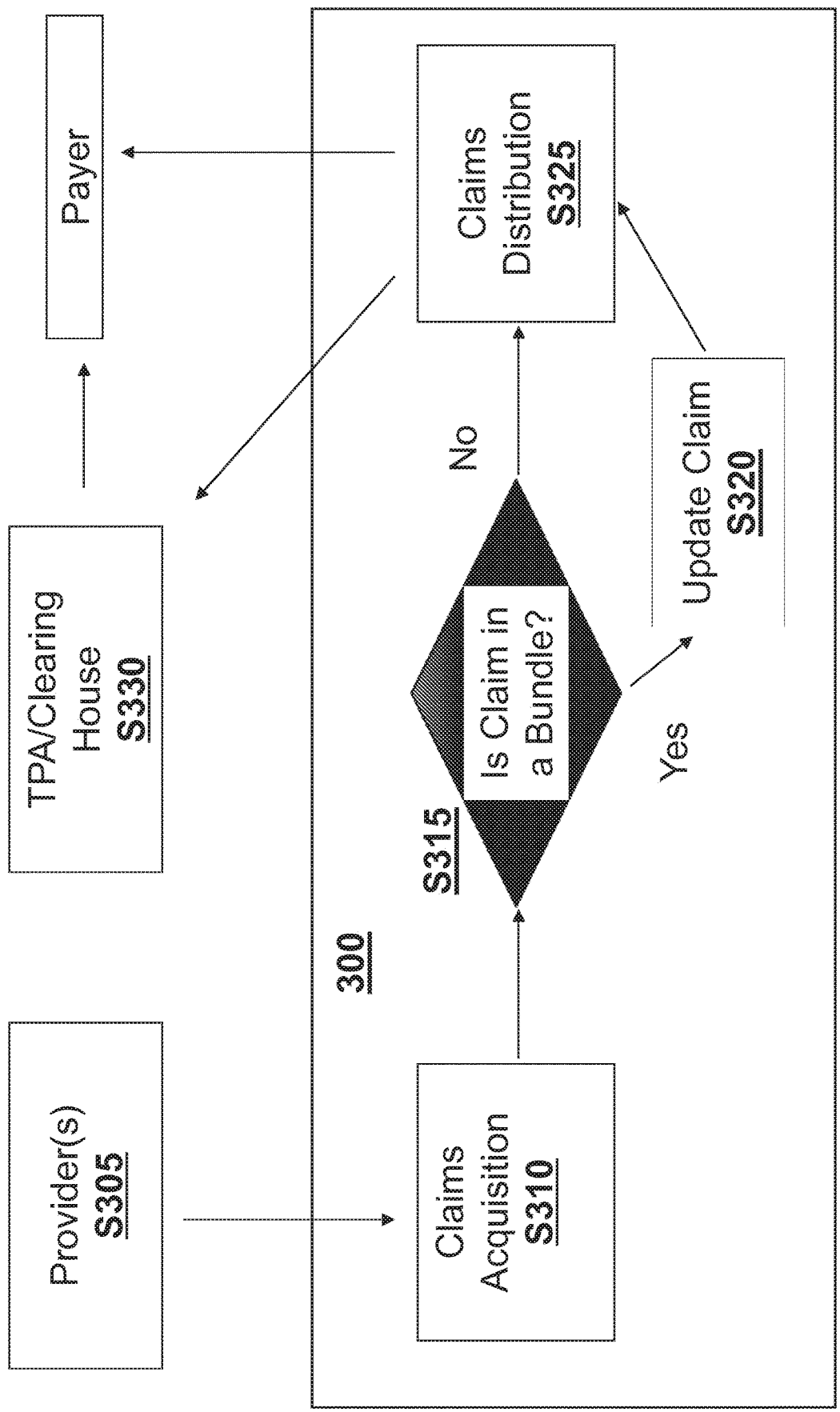
FIG. 7 illustrates exemplary process flows for pre-adjudication bundling.

A first step in the PBAS processing flow is patient episode creation (which triggers an associated payment bundle). The present embodiments are able to perform or facilitate bundling at various distinct times in relation to adjudication. A first bundling opportunity is referred to as indirect bundling and comes prior to adjudication. Indirect (or pre-adjudication) bundling occurs prior to submission of a claim to the payer. FIG. 7 illustrates two exemplary pre-adjudication bundling scenarios. In a first example, a third-party administrator (TPA) or Clearing House represents an organization that processes insurance claims, e.g., self-insured company such as employer-based plans or an insurance company. Accordingly, the TPA sits between the providers and the insurers. Where a consortium of providers have contracted to provide services under a payment bundling system, in accordance with the present embodiments the consortium of providers runs the claims through the PBAS 300 for pricing prior to sending the claim to the TPA/Clearing House. As shown, the PBAS acquires claims data from one or more providers S305, S310. The PBAS 300 determines if the claim is in a bundle S315. If YES, the claim is updated with bundle price S320 and updated pricing information is relayed to the TPA/Clearing House S325 which forwards to the Payer S330. If NO, this is relayed to TPA/Clearing House S325 which forwards instructions to pay claim under fee-for-service or per other contractual arrangement to the Payer S330. This pre-adjudication bundling is particularly advantageous for situations where there are multiple payers and direct integration between individual payer CCPSs and the PBAS system is not feasible or is lagging. One skilled in the art would realize that the above example could also not include a TPA at all, but the consortium processing claims through PBAS for pricing and sending the claims directly to the payers S325 for adjudication by the payers acting as Administrative Service Only (ASO) agents.

Another example of indirect bundling involves the provider group itself administering the bundle. In such an example, the provider group collects the claims before they are submitted to the payer and processes them through the PBAS for new pricing. Once repriced, the providers send the repriced claims to the payer and ensure that any claims that should be in a bundle are not also sent directly to the payer. Such provider-administered bundling is ideal for a provider group, an Independent Practice Association (IPA) or Organization (IPO), or a Physician-Hospital Organization PHO that wants to provider payment bundles yet their multiple payers cannot administer them or wants to administer them in different ways that cause difficulties for the provider group. When providers are administering their own bundles, the payer has a concern about the possibility of claims in a bundle also being sent directly to the payer, which would amount to a double payment to the provider. This is an example of seepage, where the payer is paying for care that should be included in the bundle but is not. In such an occurrence, the relevant claims can be retrospectively evaluated to determine if any claims were paid directly to a provider due to seepage that should have been included in the payment bundle. Once such claims are identified, the provider group would typically compensate the payer for the cost of these claims.

A second bundling opportunity arises during adjudication. The payer receives provider claims and during adjudication requests pricing from the PBAS to determine if an individual claim is part of an existing bundle or creates a patient event and triggers an associated bundle. The PBAS makes the determination and reports results to the CCPS which continues on with adjudication taking into account the prospective bundling (or not) as determined by the PBAS.

The third and fourth bundling opportunities are post-adjudication. Post-adjudication, pre-payment bundling reprices after adjudication is complete, but before payment. The results of the post-adjudication bundling do not result in a change in the pay out amount, but instead are used to create or identify potential bundles for information purposes. And, finally, there is post adjudication bundling where repricing is done entirely on the backend. The present embodiments do not operate in this fashion. Instead, the present embodiments are able to perform prospective bundling with retrospective payment. That is, the process of doing the evaluation of the claims to determine bundling is still happening during the adjudication phase, but the payer does not pay differentially at that time and instead just determines what the bundle would look like. The payment would come some time later.

While retrospective payment is known, the present embodiment describes building the bundle prospectively during adjudication, while continuing to pay retrospectively. There are numerous advantages to this model from the current art of retrospective bundling and retrospective payment. For example, feedback from the bundle creation process can alert providers to mis-utilization or quality concerns. With a process that retrospectively creates bundles, the feedback to the provider in such situations is delayed as much as a year from the time of service. In contrast, prospective creation of the bundles provides feedback as soon as the claim is adjudicated, even while the patient is still being treated in some cases. Finally, some uses of payment bundling do not impact the payment at all, but are instead used to develop episodic-of-care information that can be used by the provider organization to improve its processes and utilization. Thus, an Accountable Care Organization (ACO) that is receiving global capitation payments can still receive payment bundle information from the payer to learn how their overall delivery of services can be improved.

Regardless of when the PBAS receives the claim information for repricing, the PBAS applies specific rules in determining when a patient event is to be created in view of the claim and, accordingly, how to price the claim in accordance with a payment bundle. In addition to claim information which may trigger creation of a patient event, the PBAS may also receive non-claim information or an authorization code separate from the claim particulars that triggers creation of a patient event. The ability to create patient events from Authorizations (Utilization Management) or through pre-care notifications (such as a web-service or batch initiated by an obstetrician upon determining a pregnancy bundle should be created) is a powerful way to ensure the correct processing of claims in the first pass of evaluation. Such use of authorizations or other pre-service notifications may be fully automated through integration with a spate system for managing authorizations, it could be fully automated through the management of authorizations in the CCPS itself, it could be created through other automated systems in use by one or more providers, or it could be manually done by a user on a web form. The following general examples are illustrative. In a first example, a payer administrator specifies that a non-claim event (e.g., specific authorization code) will create the patient event and trigger the payment bundle. In a second example, while defining a payment bundle, a payer administrator specifies that a specific DRG code on a claim from a specific hospital will create the payment bundle. And in a third example, while defining a payment bundle a payer administrator specifies that a payment bundle can be created by either a specific authorization code or a web service call from the payer or a specific DRG code on a claim. In this example, whichever of these events occurs first will be used to create the patient event and the PBAS has logic for ensuring that follow-on events that would have created the patient event had they occurred first do not create a second patient event.

As described generally above, preferred embodiments include the creation of a patient event using claim information during the claim adjudication process or prior to claim adjudication through the processing of a pre-event notification, such as an authorization, through a batch or webservice data submission. Initially, and as referenced previously, the present embodiments can be implemented through a system that involves components and/or subsystems and applications that reside and/or are operated with/by different participating entities. For example, the CCPS may reside with a payer or a third-party service provider with whom the payer contracts to perform claim adjudication. The PBAS could be a system that is separate and apart from the CCPS, operated by yet another entity or it could be implemented as a subsystem and service of the CCPS product offering of the CCPS third-party service provider. One skilled in the art recognizes the arrangements that may be available for implementation.

Regarding individual claim review for the creation of a patient event, as a threshold step, the present embodiments may provide for a flag that may indicate that claims associated with a particular administrative provider are not to be reviewed for the creation of a patient event. As discussed herein, repricing may be triggered outside of the claim adjudication process (pre or post) and/or in response to non-claim events (discussed in detail below). Accordingly, one of the CCPS or the PBAS includes logic that checks this flag and acts accordingly, either by not making PBAS service calls for any claims (or subsets of claims) associated with the administrative provider or by responding to the service calls for the flagged claims with instructions to proceed with normal reimbursement (see FIG. 3, S35).

If the claim is to be reviewed for repricing, i.e., creation of a patient event during adjudication, the PBAS evaluates the claim data against each patient event definition to determine if it falls within date of service or the contract claim date is within the range. If yes, claim data is compared against defined patient event attributes/values selected from those listed previously to determine if a patient event should be created based on the corresponding attributes of the claim. The following examples are illustrative.

In a first example, through the definition of a payment bundle, the PBAS knows that a given patient event should be created whenever a claim meets the following defined attributes and values: claim is for a specific Healthcare Common Procedure Coding System ("HCPCS") code service; the place of service and the provider type is free-standing diagnostic center; a modifier for the procedure code is in a predetermined list of modifier codes; and the claims date of service is after the effective date for this payment bundle with the identified administrative provider. Accordingly, the PBAS evaluates each claim (subject to initial filtering for inclusion in a pre-existing bundle) against these specific values to determine if a patient event has occurred.

In a second example, through the definition of a payment bundle, the PBAS knows that a given patient event should be created whenever a claim meets the following defined attributes and values: a specific APC code service; the patient is between the age of 8 and 60 at the time of the date of service; the allowed charges is greater than $1000.00; and the claims date of service is after the effective date for this payment bundle with the identified administrative provider. The PBAS evaluates each claim against these specific values to determine if a patient event has occurred.

Once a claim is determined to create a patient event there is no need to further process that claim against patient event rules/definitions. For example, the PBAS receives a claim and the claim is subject to evaluation against a list of three patient events, i.e., against the defined attributes and values for each, wherein creation of any one of the patient events triggers a specific payment bundle. While evaluating the second patient event business rule, the PBAS determines that the claim should create a patient event. The PBAS does not process the claim against the third patient event business rule. In a less typical instance, processing on the claim might continue and if the claim were found to qualify for inclusion in multiple patient bundles, it would be wholly included in one of the eligible patient bundles based on business logic, or it might be apportioned among multiple patient bundles based upon business logic for the apportioning.

As discussed, non-claim event either from the CCPS or non-CCPS data feeds can create patient events separate from evaluating claims during claim adjudication. In a first example, an obstetrician uses a payer portal to indicate that a specific patient is starting a patient bundle for pregnancy on a specific date. In a second example, a hospital sends SOA-based web service call to the payer indicating that a specific patient is starting a patient bundle for heart bypass surgery on a specific date. In a third example, a specific CCPS approves an authorization for an AICD implantation for a specific patient at a specific hospital on a specific date. The CCPS creates a web service call to notify the PBAS about the authorization. The PBAS evaluates the authorization and determines that this authorization is a patient event, based upon business rules evaluating, e.g., the authorization type, group information about the member and the provider ID. The PBAS has the ability to manage and process files, including batch feeds, of different sources and different formats, including ASCII, XML, and X12 278. The payer may pre-process the data feeds to determine if the content of the feed are acceptable, such as an authorization or other approval or evaluation process, prior to submitting the feed to the CCPS.

The non-claim administrative data feed will need to include the minimum amount of information required to create a patient event, including: the source of the patient event and the caller entity (such as a specific provider or the CCPS); Patient ID; Anticipated date (for some patient events this will be the date of service or some primary procedure or major event and for others this will be the approximate start date of the patient bundle). By way of example, an authorization from a hospital for a bariatric surgery includes the specific date of the surgery. The definition of the patient event knows that this date should be used to create the date window for the patient bundle. And as an alternative example, a web service call from a hospital for a heart bypass includes the expected date of admission, pending a patient achieving certain lab results. The defined patient event logic recognizes this date is estimated and should only be used to create the date window for the patient bundle until the actual date of service is known from a claim, at which time the PBAS revises the date window.

The non-claim administrative data feed may indicate a specific payment bundle type code. By way of specific example, a web service call from an ophthalmologist is used to indicate that a payment bundle for cataract surgery of the left eye should be created for a specific patient on a specific date. In addition to the patient ID and the date, the web service includes a payment bundle type code that was defined by the payer for this payment bundle, a value equal to the primary key of the payment bundle in the system. This type of patient event definition is useful for this type of payment bundle where it is difficult to discern the stop of a cataract surgery of the right eye from the start of the cataract surgery of the left eye. A separate web service call with payment type code and other identified information would be made for the right eye.

Alternatively, the data feed may indicate a code (such as an authorization type) which can be mapped to a patient event for a specific payment bundle. The administrative provider ID may be part of the mapping. In either case, the administrative provider is indicated. For example, an authorization from the hospital for a hip replacement is processed through the CCPS. Once approved, the authorization is furnished to the PBAS. The definition of a patient event for hip replacement includes the identification of this authorization using the authorization type code that indicates this authorization for hip replacement. In another example, a cardiac surgeon uses the web portal to create a patient event for an AICD implantation for a specific patient on a specific date. The data entered into the web portal includes the identification of the hospital where the procedure will take place. The hospital, not the surgeon, is the administrative provider for this payment bundle and the surgeon is contracted to do payment bundling at multiple hospitals.

A non-claim administrative data feed may include a status flag instructing the system to change information about a previously created patient event. This may override existing information with better information (expected date of procedure) or change the status of the existing patient event. For example, a hospital had previously submitted a batch file containing a row that created a patient bundle for a patient on a specific date. Subsequently, the hospital submits another batch file containing a row that instructs the system to change the status of a previously created patient bundle, since the patient has died before the payment bundle was completed. Another reason to modify a patient bundle could be a changed diagnosis or the presence of a specific co-morbidity. With the change in the patient bundle, it may be necessary to reprocess the impacted claims and pay them fee for service, which the PBAS of the present embodiments is able to determine and communicate to the payer.

The PBAS is also able to track when a patient event has already been created by a first non-claim event (or claim) and not create a second patient event when a different non-claim event (or claim) is received. For example, the PBAS logic determines that a patient event can be created by either the surgeon or the hospital involved with a knee replacement bundle, either of which can send a non-claim event to start the payment bundle. For a given patient, the surgeon may send the non-claim event first for a patient and start the payment bundle. A second bundle is not created when the hospital subsequently sends a non-claim event for the same patient for the same payment bundle within the range of dates established by the first non-claim event.

Once the PBAS identifies an instance that should trigger the creation of a patient event, the PBAS processes the patient event. As referenced previously, an initial patient event processing step is to resolve complexity if a patient event already exists for a specific patient. This includes suppression or avoidance of redundant (multiple) patient bundles. A redundant patient bundle would occur if a patient had more than one bundle of the same type for the same date range. For example, a hip replacement payment bundle has two different patient events, either one of which can start a patient bundle. This hip replacement payment bundle has a patient event based on claims with a specific DRG as well as a non-claim event using a specific authorization; either of which would trigger the payment bundle. For a given patient, the authorization may occur first, creating the patient bundle. Subsequently, a claim is processed for the same patient with the triggering DRG. In this scenario, the PBAS does not create a second bundle for the patient based on the DRG code. Instead, the PBAS recognizes that the second claim is part of the establish bundle and prices accordingly.

In creating a patient event based on claim or non-claim data, the PBAS assigns various identifying attributes to the patient event in order to process future claims for exclusion therefrom or inclusion therein (and pricing in accordance with triggered payment bundle). Such identifying attributes include, but are not limited to: assignment of a unique identifier for each patient event; Claimant (also referred to as Patient); Payment bundle; Bundle type (Hip, Knee, etc.); Dates (admission, discharge, and procedure); Date range for claim inclusion; Payment indicator that determines the system processing status of the claim(s) that pay the bundle; Administrative Provider; Patient event status (Regular, Incomplete, Complete, etc); Method of how the patient event was created.

The PBAS recognizes that any single claim can only be assigned to one patient bundle. For example, a single patient could have more than one active patient bundle. The PBAS is able to determine which patient bundle the claim belongs to and that it need not evaluate this claim for inclusion in the remaining patient bundles. In the alternative, the PBAS may assess the claim against multiple patient bundles and assign it to one or more than one patient bundle as described above.

With the creation of the patient event and triggered payment bundle, the PBAS is not only able to reprice a triggering claim and future, subsequent claims within the bundle, it can also reprocess past claims. Accordingly, the PBAS checks the patient's previously processed claims to see if any fall within the event date window. Those claims will then be examined to determine if they should be included in the patient event. Any claims that should be included in the patient event will then need to be re-adjudicated. Additionally, if changes to certain details of a patient bundle are made after initial creation and claim processing in accordance therewith, the PBAS can determine which claims need to be reprocessed. Further, the PBAS automatically reprocesses certain claims after the passage of a certain amount of time. Reprocessing allows the system to take corrective action based upon new information available and react to new details by making changes to the payment bundling processing that has occurred to date.

The following examples illustrate various reprocessing and repricing scenarios based on the creation of a patient event. In a first example, a claim is processed on the March $2^{nd}$ from Anesthesia-R-US for a patient for anesthesia services delivered on March $2^{nd}$ at ABC Hospital. This claim does not match any active patient events and does not start a patient event, so it is paid normally by the CCPS. On March 5th, a claim is processed from ABC Hospital for a specific DRG for the same patient. Based on the patient event definitions for a hip replacement payment bundle, this claim indicates that a bundle should be created for the patient. The anesthesia provided on March $2^{nd}$ should be part of this patient bundle, but that claim has already been processed. It is necessary to reprocess that claim so that it can be correctly added to the patient bundle.

In a second example, on March 1st, a patient sees their primary care physician complaining of knee pain. The physician orders a diagnostic test for March $3^{rd}$. There are three claims created already, the office visit with the primary care physician, the diagnostic test, and the reading of the diagnostic test. At this point, there is no active patient event and no one knows that this might be a knee replacement. These three claims are all processed normally by the CCPS since none of the single claims met the patient event definitions for a particular payment bundle. On March 6th, the physician determines that a knee replacement should occur March 15th at Hospital ABC. On March 8th, the physician sends a non-claim administrative data feed to the PBAS regarding the upcoming procedure and the estimated date of the 15th. The system creates a patient event from this feed for the patient. The payment bundle definition indicates that certain types of diagnostic expenses that occur up to 15 days before the procedure should be included in the bundle. Accordingly, it is necessary to reprocess all the claims for this patient that occur 15 days before the anticipated procedure date of the 15th—including the original three claims for the office visit with the primary care physician, the diagnostic test, and the reading of the diagnostic test—to see if any of them should be included in the bundle.

Reprocessing may also be necessary when a patient event is manually deleted. For example, while reviewing data in the PBAS, a payer administrator realizes that a configuration rule was set incorrectly and a patient event was created in error for a patient. The payer administrator deletes the patient event. All claims processed as part of the patient bundle need to be reprocessed so that they will either pay normally or be correctly placed in any other patient bundles for that patient.

Similarly, reprocessing may be necessary when a patient event is cancelled, either manually through a user interface application (See, e.g., FIG. 1, 25) or through the processing of a claim or a non-claim event. For example, a hospital sends a non-claim event that creates a Lap Coli patient episode for a patient, based upon an authorization. After 4 weeks, the hospital realizes that the patient is not going to get the procedure and sends another non-claim event cancelling the patient bundle for this patient. Any claims processed as part of the patient bundle need to be reprocessed so that they will either pay normally or be correctly placed in any other patient bundles for that patient.

Reprocessing also may be necessary when there is a change of any attribute of an existing patient event that could impact the assignment of claims to a patient bundle. Again, the change may occur either manually through a user interface application (See, e.g., FIG. 1, 25) or through the processing of a claim or a non-claim event. By way of example, on the March 20th, a claim is received from the surgeon that is included in an existing payment bundle. The claim data also shows that the procedure occurred on March 18th, not the estimated date of the 15th. The actual date of the procedure is updated in the Patient Event field. Because some of the claims that had been included in the payment bundle may now be more than 15 days from the date of the procedure—which is the inclusion date window—they may need to be excluded from the procedure and paid normally. In particular, the office visit that occurred on March 1st is now outside of the updated date window for this patient event and should be processed outside of the bundle.

Finally, a plan administrator could specifically indicate that a patient bundle should be reprocessed. This indication can be received through a user interface application (See, e.g., FIG. 1, 25).

The process for reprocessing claims for one or more patient events where changes to the one or more patient events either creates a patient event or alters the date window includes analyzing all claims in the new processing date window plus all claims currently included in the patient bundle. By way of example a payment bundle definition states that the date of the procedure is the date from which a date window is created. It further specifies that all claims for potential inclusion in this payment bundle must occur in a date window of 15 days prior to the procedure date and 40 days after the procedure date. In the initial version of the patient event, the estimated date of the procedure was the March 15th. It is later determined that the correct date for the procedure is March 17th. In creating the date window, the window should start with the date that is 15 days prior to the 15th (using the earliest version of the start date) and end with the date that is 40 days after the 17th (the latest version of the end date).

In a second example, a patient event is created on March 22nd for a patient. The starting date of the patient bundle is the 20th. The payment bundle definition states that claims 10 days prior to start of the bundle may be included in the bundle. The PBAS would reprocess any claims for the patient that occur 10 days prior to March 20th through March 22nd to see if they should be included in the new patient bundle.

In a third example, a patient has one existing patient event that has a date window of March 2nd through March 25th. A claim creates a new patient event that starts on March 15th and should last until March 30th. All claims between March 2nd and March 30th (or the current date) should be reprocessed.

In a fourth example, a patient has a patient event that started on March 5th and could include claims 3 days earlier. On March 25$^{th}$, it is determined that the patient event will be canceled. All claims for the patient from March 2nd to March 25th should be reprocessed.

In order to implement the reprocessing, the PBAS identifies all claims for the patient in the specified date range. This information can be identified by accessing the CCPS or if claims cannot be accessed, the PBAS can log the claims (or the criteria for claims) that should be reprocessed, for subsequent manual review or re-adjudication. Once the claims are identified, the PBAS reprocesses against the existing patient bundles, adding or removing claims from the patient bundle as necessary and ensuring any changes to claim pricing are reported to the CCPS. For recordkeeping purposes, the PBAS maintains a list of the results of the claims that were identified to be reprocessed.

The claim information provided to the PBAS by the CCPS for processing can be a subset of the claim information that is initially provided to the CCPS for processing by an individual provider, administrative provider or contracted representative thereof. One skilled in the art understands that individual claim submissions can include numerous details that are not required for processing. The present embodiments require certain claim data, if applicable, be received by the PBAS in order to perform the processes described herein. The required data for processing is dependent upon rules configuration. For example, if rules are defined where payment bundles can be specific to an employer group, then group is required. Whereas, if payment bundles will apply to all employers, employer group is not required. Additional data, if provided, would be useful to the processing, but is not necessarily required. Required data from the claim header includes: Claim number; Claim type; Contract ID (i.e. Agreement ID); Patient Gender; Patient Age; Patient Account Number (Patient ID); Provider Type; Admission date; Admission type; Discharge date; Discharge status; Type of Bill; Statement From Date; Statement To Date; Procedure Code Type; DRG code; Procedure code (multiple)—ICD9 and ICD10; Procedure date (multiple); Diagnosis Type; Diagnosis—ICD9 and ICD10; Diagnosis; Claimant ID (both the Member ID and Member Contrived Key); Group; Subgroup; Class; Plan; and Product. Required data from claim line detail includes: Line Number; APC code; Allowed charges; Total charges; Original considered charge; Service from date; Service to date; Units; Procedure Code and Pricing Explanation. The PBAS also requires Provider Specialty.

Other claim data that should be included if available, but may not be necessary for processing includes: Provider Related Facility; Admission source; Modifier; Additional Modifiers; Place of Service; Service Type; Group Charges; Group Units; Allowed Amount; Allowed Units; Plan Not Covered Charges; Revenue Code; Diagnosis Pointer; Provider ID; Provider Name; Provider NPI; Provider Network ID; Override Line Number; Override Code; Override Amount; Override Value; Override Date; Override By; Explanation; and Auto generated override indicator.

In response to the CCPS sending a request to the PBAS, the PBAS responds back to the CCPS with at least one of the following messages: claim not impacted by payment bundling (process normally); claim should be re-priced (Accept changed Allowed Charges); or delay the claim. The latter occurs in those circumstances wherein there is not yet sufficient information to know if a claim is in a bundle or not. The use of a "Delay" response for the claim asks the processing system to delay payment of the claim for a set period of time. The PBAS may return a response that includes various amounts of information from all claim line and line level pricing details to simply the updated price and an explanation of code. For example, the PBAS response may include the following data: Group Charge; Group Units; Allowed Amount; Explanation Code; and User Message.

In addition to response messages, in preferred embodiments, the CCPS is able to receive service calls. This is an original call (e.g., web-service call) made from the PBAS to the CCPS. The substance of such service calls may include, for example, claim reversal, i.e., PBAS determines that a claim that was paid should not have been. A service call could be a claim adjustment, i.e., PBAS determines that the amount paid on a claim is incorrect. This can include the functionality of the claim reversal requirement above. A typical use case would be to pay a claim previously set to no-pay in error. Yet another service call is a reprocess claim call. This is a way to undo the delay option discussed above, where the claims system should reprocess a claim that was previously set to a "delay" status.

Further still, claim data received and processed by the PBAS may trigger a message that should be reported back to the sending CCPS. For example, during claim processing the PBAS knows that claims for anesthesia in a given CPT range must be provided by providers included on a specific list of provider IDs. If a claim is processed for one of the CPT codes for a patient with an active patient bundle, but the provider is not on the list, the claim produces a message back to the core claim system. The message identifies that the claim probably should be included in the bundle, but an examiner needs to inspect the claim to be sure. The claim should be pended in the CCPS and routed to an examiner for review. At a future point in the time, the examiner will resubmit the claim for processing, once the situation has been resolved. In a different scenario, the PBAS system may be reporting an error back to the CCPS.

As discussed above, the CCPS also has the ability to send various data feeds—separate from claims—to the PBAS. The data feeds can include lists of claims. When doing the periodic processing, it is important to have all of the most up-to-date claims for a date range for a specific patient in view. The PBAS needs to call for a list of claims for a patient in a date range and get a data feedback, the data elements are the same as those listed above. The CCPS can also send authorizations. One standard method of determining a patient event is to recognize a specific authorization as discussed above. The CCPS also provides lists of providers (including provider IDs) so that the PBAS has an up to date listing. Further still, the CCPS may provide lists of patient hierarchy to provide a valid listing (i.e., group, subgroup, class, plan, product; those implementation-specific lists of ways patients are sub-divided organizationally).

To this point, detailed description has been provided of the processes for modeling bundles, contracting between providers and payers to accept bundle payments (including subcontracts between administrative providers and individual providers), defining patient events that trigger payment bundling, proactive bundle creation during adjudication based on claims, non-claim events or other data feeds from CCPS or external feeds (e.g., web portal application to PBAS), and reprocessing claims based on various changes. The following provides various examples of the actual payment scenarios resulting from PBAS determination that a claim is part of a patient event and associated payment bundle.

In a first typical example, the payer CCPS receives a claim from a provider as a normal fee-for-service claim. During the claim's adjudication, the CCPS prices the claim. After the CCPS prices the claim in accordance with normal fee-for-service pricing (and any adjustments for specific contracts between the payer and the provider), the CCPS requests a check against the payment bundling logic at the PBAS to determine if the claim triggers a patient event for payment as part of a payment bundle or is to be included in a triggered bundle. There are a number of ways a claim might be paid differently from fee-for-service.

In a typical bundled payment approach, a single payment is made at the time of service for multiple services by multiple providers over multiple days. In operation, this typically means that for all but one claim that is part of a payment bundle, the pay out is $0. And for the one claim that is designated to trigger the payout for the entire bundle, the payout price could in fact be for more than this single claim's requested amount. Take the following example, a hospital is one of multiple providers in a payment bundle and is also the administrative provider whose claim triggers the full payout for the entire bundle. Even though the fee-for-service amount for the hospital provider's services to the patient would normally be priced $7,000 under fee-for-service rules, since the hospital's claim actually triggers full payment for all services by all providers under the payment bundle so the claim is priced at $10,000 for all of the episode. The additional $3,000 is paid out to other providers under the terms of the contracts with the administrative provider. More particularly, following this example, the other service provider is a surgeon who submits two claims to the payer, one for the surgery performed at the hospital, which is normally paid at $2,500, and one for the follow-up care which is normally paid at $500 under fee-for-service rules. However, because this care is in the episode (and the compensation for the surgeon is included in the single episodic payment), both of these claims would be priced to zero. The surgeon's $3,000 would be paid out of the single $10,000 payment made to the hospital in response to the payment bundler triggering claim.

There are variations to this example which will be appreciated by those skilled in the art, some of which are described above with respect to various modeling scenarios. For example, the non-triggering claims, e.g., the surgeon's claims in the example above, could be priced at a fee other than $0. This way the surgeon receives some portion of fees from the payer and the remainder from the administrative provider after the payment bundle episodic payment has been paid and distributed.

As an alternative to paying at the time of adjudication, i.e., prospectively, in accordance with the payment bundling pricing, the present embodiments can also facilitate retrospective payments in accordance with payment bundling. For example, the payer pays all claims under fee-for-service rules, but still submits the claim information to the PBAS. Under this retrospective embodiment, submission of claims to PBAS in batches instead of during individual claim adjudication is likely preferred since adjudication does not need to wait for a response. But either is acceptable. The PBAS remembers what the payer paid for each claim, analyzes the claims as described above for episode triggering and payment bundling and provides the payer with "truing up" details. Depending on the payment bundle rules, the payer could end up giving more money to individual providers as or taking money back from individual providers. Accordingly, under this embodiment, the payer could still determine episodes at the time of adjudication even though not repricing at that time.

In a further alternative scenario, the PBAS may indicate a withhold pool situation, wherein, for example, the payer would initially distribute 80% of the bundled allowed amount to the participating providers as claims are submitted. Then 90 days after the episode is deemed complete, the payer may distribute the remaining 20% if certain financial conditions were met.

In addition to the numerous episode creation, processing, pricing and reprocessing examples described to this point, there are myriad of variations and extensions of thereto. The following are representative of particular situations contemplated by the embodiments described herein.

In some instances, the PBAS does not receive enough information from a claim to make a final determination that the claim should be included in a payment bundle. But the PBAS logic knows based on various attributes of the claim that it likely should be part of a bundle. For example, the PBAS receives a claim from anesthesiologist, which likely is included in a hospital bundle, but PBAS cannot confirm until the hospital claim comes in for the corresponding surgery. For these cases, the PBAS treats the anesthesiologist's claim as a provisional claim and sends a return message to the CCPS to "hold" or suspend processing (also referred to as "suspend," "pend" or "drag"). In a drag scenario, the payer can go ahead and price under fee-for-service, but do not pay for a predetermined number of days because anticipating a second claim from hospital will trigger payment bundle. In a suspend/pend scenario, the claim is routed to a queue in the CCPS, where it is held until some action is taken upon it. The CCPS would remember the claims and that the pend occurred. One of two events would cause the PBAS to request that the CCPS unpend the claim. The first event is the creation of a patient event. As discussed elsewhere, when a patient event is created, all the claims in a date window can be reprocessed to determine if other claims should be included in the newly created patient bundle. The second event is the passage of time; once a number of days (established as a setting in the business rules) has passed and no related patient event has occurred, the PBAS indicates to the CCPS that the claims should be reevaluated. Failing to match a patient bundle, the claims would be paid normally. It is also possible for a CCPS to be able to take an instruction on how to process the tended claims without requiring that the claim be send to the PBAS a second time.

The PBAS logic has the capability to recognize serial and concurrent episodes for a patient that might otherwise appear to be in a single bundle. This error would result in delay and underpayment to the individual providers since the payer would only pay out the amount for a single bundle. An example of concurrent episodes is instance where multiple procedures are performed in single operation, e.g., during one back surgery, multiple stents are inserted at a time. Depending on the episode definition, each stent procedure triggers a separate bundle and accordingly, a separate payment. Similarly, an example of serial episodes are cataract surgeries, wherein the episode and thus bundle is defined as single eye (note that a single episode could be defined to include both eyes, in which case the serial bundling is not an issue). If patient is having both surgeries done in serial and there are multiple bundles, it can be difficult to determine when the first bundle ends, e.g., for the left eye, and the second bundle begins, e.g., for the right eye. For example, patient goes for follow-up on left eye post-surgery which should be included in a first bundle and at the same appointment is prepped for right eye which should start second bundle—how does payer know where the first bundle ends and the second bundle begins? The business rules available in the PBAS may be used to establish the processing logic to be used.

The PBAS has configurable logic for creating specific business rules to process and separate out the serial bundles and the concurrent bundles.

The PBAS also includes configurable logic for determining not only when to bundle, but when not to bundle or rebundle, when to unbundle and when to end a bundle. For example, while there are instances where certain claims never create a patient event (and are never included in a bundle), there are other situations where a claim that would normally create a patient event or be included in a pre-existing bundle should not create the event or be included in the bundle. Exemplary situations include: patient death; patient passes out of eligibility or overall price of bundle becomes too high. Take a specific example, patient event has been created and pursuant to rules, PBAS has been zeroing out claims that are part of the bundle and a claim comes along that indicates that there should not have been a bundle at all (the intent is to exclude patients with cancer; at the time of the patient event, it was not known that a patient had cancer, but a subsequent claims includes the diagnosis of cancer). In this case, it is necessary to cancel the bundle. PBAS is able to reprocess the claims previously included in the bundle and pay them as normal fee-for-service as described previously herein. PBAS is also able to avoid creating a new bundle when another claims that would have been part of the canceled bundle comes in.

As discussed previously, not all claims are necessarily submitted to the PBAS for processing against payment bundling logic. Accordingly, there can be a filtering application applied at the CCPS prior to making the web-service call to the PBAS to essentially rule out claims that are clearly never going to be part of a payment bundle. In this instance, the PBAS receives a subset of payer claims that have already been through a first payment bundling filter. Once received at PBAS, the episode creation and inclusion logic described herein is applied (See, e.g., FIG. 3, S10-S35). As described, in cases where PBAS determines that a claim is likely in a payment bundle, the PBAS records this fact, generates metadata and in most cases changes the claim price from fee-for-service to $0 (or to 100% of the bundle payment upon receipt of the administrative provider payout triggering claim or other designated payout triggering claim). While this is the common claim processing result for claims received by the PBAS, there are variations.

The PBAS logic is able to account for special cases where a service that is included as part of an episode and triggers pricing under a bundle is performed by a provider that is not part of the bundle contract. One skilled in the art recognizes this situation as leakage. The following example is illustrative of a leakage scenario and a process for handling pursuant to the embodiments described herein. Hospital A (the administrative provider) contracts with a payer to accept a bundle payment of $10,000 for patient episode A that will include services from the Hospital A, surgeon A (included provider), and rehabilitation center A (included provider). Instead of using rehabilitation center A, the patient uses rehabilitation center B, which is not part of the bundle. Rehabilitation center B submits a claim to the payer and the payer forwards relevant information to PBAS. In this situation, the PBAS recognizes that this claim should have been included in the bundle for patient episode A and priced to $0, but since the service was performed by a provider outside of the contract group of included providers, the PBAS tells the payer to pay at fee-for-service rate (example, $1,000). Accordingly, without PBAS tracking and adjustment, the payer will pay Hospital A $10,000 when the patient episode A payment bundle triggering claim is received and an additional $1,000 to rehabilitation center B. The payer will essentially over pay by $1,000.

In the above-described example, the PBAS tracks the overpayment and reports to the payer so that the payer can adjust the $10,000 bundle payment. If the patient episode A payment bundle triggering claim has not yet been received, the payer can reduce the $10,000 payment to $9,000. If the $10,000 has already been paid out, the payer uses other mechanisms in order to recoup the over payment, e.g., reduction in future payments on different patient episode bundle payments. Such reduction may be one automatically by the PBAS or through a manual process driven by data from the PBAS.

This scenario puts the risk on the provider group to steer patients to bundled providers and reduce leakage. Following on the example above, the PBAS is able to recognize and analyze out of group claims, process and perform actions that impact potentially related patient events and corresponding payment bundles and payouts. There are other examples of situations wherein during adjudication the payer wants to pay 100%, e.g., unforeseen events. The following specific example is illustrative. A patient has surgery for unanticipated reasons. While the underlying surgery and certain related services are part of a defined patient event, in this particular example, the patient requires a lot of additional services that were not meant to be included originally in the episode and resulting payment bundle. Under this circumstance, the payer goes out of pocket to pay these extras separately at 100% under standard fee-for-service as the additional service claims are received. The PBAS tracks these additional claims as part of the patient episode and still pays the original bundle amount when the triggering claim is received. Here, the payer takes the risk and is not going to seek reimbursement by read-justing the original bundle amount.

Yet another alternative to the payment bundle payment scenarios described thus far is the ability to facilitate reference pricing. For reference pricing, instead of having all claims except the trigger claim paid at $0 and the trigger claim paid at 100% for the payment bundle, the payer agrees to pay a capped, fixed amount for episode services. The PBAS is able to create a patient episode as described herein and then pays 100% on claims within the episode until reaching the cap. Once the cap is reached, the payer pays $0 on other claims in the bundle and the provider group will need to seek payment from the patient.

In addition to those discussed herein, the present embodiments facilitate bundle revisions based on newly received information. For example, the PBAS can increase the total bundle payout or other flat fee pricing based upon business rules. For example, a patient episode could evolve to include additional, fewer or different services based on changing patient health or identification of a particular patient attribute at patient episode creation. The patient episode definition could have a starting payout for the corresponding payment bundle of $10,000 for a patient meeting certain health criteria. As claim information is received, it the PBAS identifies information that shows that the patient is morbidly obese, the payout could be increased by a certain percentage (%), e.g., 10%. Similarly, if it is determined that the patient is hypertensive, the payout would be increased another 15%. These increases would be in accordance with pre-established business rules established during payment bundling administration (See FIG. 2). The increases reflect an assumption that additional services will be required in view of these patient conditions.

Similarly, there could be decreases in the bundled payout percentage (%) for a patient episode if a patient is in better health or presumed to be in better health, e.g., based on age or the like. For example, a patient for a hip replacement would likely be in a certain advanced age range and would require, on average, more rehabilitation than a much younger recipient. The hip replacement bundle would be default priced for the older recipient to include a higher payout due to the increased rehabilitation required. When the PBAS receives data that the recipient is actually younger, the payout can be adjusted according to pre-established business rules.

Similarly, there could be a change to the bundle price based on the creation of supplemental data. Consider the example of a knee arthroscopy. This procedure may be intended to prevent a more expensive and serious procedure, a full knee replacement. Thus a surgeon may be paid $1500 as a bundle price for an arthroscopy bundle. However, if a knee replacement does occur, the knee replacement is not part of the arthroscopy bundle, but the claim for the knee replacement is supplemental data that indicates an unintended outcome. As a result of this unintended outcome, $500 of the $1500 is taken back from the surgeon doing the arthroscopy. This is accomplished as follows: when the knee replacement claim is processed, its price is not changed, but it does create a supplemental data indicating that a knee replacement occurred and that claims in the patient bundle should be reprocessed. When the claim for the arthroscopy is reprocessed, instead of paying the bundle price of $1500, the rules indicate that only $1000 should be paid if there is supplemental data for a knee replacement.

Further still, the PBAS can apply logic to increase or decrease payout based on, for example, patient readmission for relapse, more or less physical therapy, etc. The PBAS is also able to instruct regarding payments made to the provider through member liability and has the ability to deduct received co-pays from the payment bundle payout amount since providers already received from members. The payer should not have to pay the amounts that members already covered through co-payment.

An additional feature of the preferred embodiments is the ability of the PBAS to identify, generate, categorize, flag additional information of/from the claims data which is useful for later processing. This functionality allows for adjustment of bundles or the analysis of bundles. For example, if a claim comes through that identifies that a patient had surgical site infection, the PBAS creates metadata or supplemental data (hereafter "supplemental data") regarding this fact and flags the claim. Accordingly, this allows attributes to be created or changed about bundles. As discussed above, this information may change the way a created patient episode is treated by the business rules being processed that can react conditionally based on the supplemental data. A new attribute determined from the supplemental data can be fed back into the rule engine and can change/adjust the underlying business rules for an entire category of patient episodes and corresponding bundle payout amounts or other actions related to a bundle, e.g., time periods, when to blow-up, etc. Further, the supplemental data is an important input into modeling and allowing the variation in utilization or morbidities to be modeled. Finally, it may be used as a means of measuring changes in care quality.

The types of supplemental data include: Date Milestones; Performance and Roles. Data Milestones are dates that may or may not impact the dates of the patient event. These may or may not impact the dates of the patient event. This information may be stored as Date value or date range, Date Milestone Type and associated Claim ID. Examples of Date Milestone data include start date of readmission, end date of readmission, start/end of warranty. Performance data is quality or utilization information about a claim. This information may be stored as Performance Type and associated Claim ID. An example would be that fact that there is a surgical site infection. Roles data categorizes the claim as playing a specific role in the bundle. This information may be stored as Role Type and associated Claim ID. An example would be that fact that the claim is anesthesia or post-discharge. There is no limit to the supplemental data definitions that may be created and the supplemental data definitions can be reused with other payment bundles.

Supplemental data may trigger the reprocessing of claims. The following examples are illustrative. In a first example, after a claim for a surgeon doing a lap coil has been evaluated for inclusion and determined to be included in a patient bundle, any supplemental data rules are evaluated. In this case, business logic determines that the claim has a performance type of Laparoscopic, based on the specific CPT code used as well as a role of Surgeon Fee.

In a second example, a member has an appendectomy patient event with a bundle start date of January 1st and a bundle end date of January 30th. A claim is processed on February 5th with a date of service of January 20th and a diagnosis code indicating that claim is for treating a surgical site infection. Based on this claim, the end date of the patient event is changed to 45 days after the date of the infection, or March 4th. Claims are reprocessed accordingly, to determine if additional claims with a date of service after January 30th that have already been processed (and were outside the date window for the patient event) should now be included. In this second example, the supplemental data was used to update a date that is stored in the patient event. Accordingly, the supplemental date data in this instance need not be stored separately as it now becomes part of the updated patient event information. Examples of patient episode date attributes that may be updated based on supplemental data include: Admit Date, Procedure Date and Discharge Date.

As an example, a standard date window for the inclusion of claims might be 90 days. However, if a readmission occurs, the date window might be extended to a period 6 days after the discharge date of the readmission.

As described briefly above, supplemental data can be used as an input when evaluating claims for inclusion in a patient episode or creating other supplemental data. The following examples are illustrative. In a first example, three days after ascertaining supplemental Date Milestone data including start/end dates of readmission, a subsequent claim for this patient from Surgeon A has a claim inclusion rule that requires that any claim for the surgeon, occurring during the date range start of readmission and end of readmission, should be included in the bundle, but paid 30% of the allowed amount. Accordingly, the occurrence date is checked against the supplemental Date Milestone data to determine if the revised payout is applicable.

In a second example, fifteen days after ascertaining supplemental Performance data of Readmission, a subsequent claim for this patient from the skilled nursing facility has a claim inclusion rule that requires that any claim for a skilled nursing facility should be excluded from the bundle if there is a Performance type of Readmission. Accordingly, this claim would be excluded from the bundle.

In a third example, five days after ascertaining supplemental Performance data of Revision and Date Milestone data including start/end dates of readmission, a subsequent claim for this patient from a surgeon that was asked to give a second opinion. This claim is processed against a patient inclusion rule that requires that any claim for a surgeon, occurring during the date range start of readmission and end of readmission, should be included in the bundle but paid 100% of allowed charges if there is already a claim of type Revision. Accordingly, the occurrence date is checked against the supplemental Date Milestone data to determine if the revised payout is applicable since the supplemental Performance data is Revision.

To this point, the process has been described wherein payment bundles are identified and prospectively created and claims are re-priced accordingly. An important next step is the unbundling of the bundled payment and distribution to the individual providers. Depending on the contract arrangements, this step could be performed by the payer, the administrative provider or some other contracted administrative entity. The following example is but one of a limitless number of possible payout scenarios that conveys the unbundling and payment concept of the present embodiments. In this example, there are two providers, Hospital A and Physician A, who are to share the single, episodic payment from the payment bundle. In this particular example, the hospital saved $1,000 on a particular patient's costs, which translates into a $1,000 profit. The bundle payout is $10,000. The hospital pays the physicians the $3,000 total they are owed because of their utilization plus an additional $500 representing 50% of the $1,000 profit. The hospital retains $6,500, which is $500 less than the fee-for-service payment (which would have been $7000 for the services provided by the hospital), but Hospital A's costs were $1,000 less, so they also benefited from the savings. Referring to FIG. 6 and descriptions above, the present embodiments describe logic for modeling and implementing unbundling and payout using a payment disbursement calculator (PDC) that calculates the amount of the payment bundle amount to be paid out to each participating provider.

In implementing these systems and methods to be performed by a suitably programmed computer, it is intended that the computer have a processor and a computer readable medium, wherein the computer readable medium has program code. The program code can be made of one or more modules that carry out instructions for implementing the systems and methods herein. The processor can execute the instructions as programmed in the modules of the program code.

The systems and methods described can be implemented as a computer program product having a computer readable medium having a computer readable program code embodied therein, the computer readable program code adapted to be executed to implement a method for performing the methods described above. Each step or aspect can be performed by a different module, or a single module can perform more than a single step.

The systems and methods described herein as software can be executed on at least one server, though it is understood that they can be configured in other ways and retain its functionality. The above-described technology can be implemented on known devices such as a personal computer, a special purpose computer, cellular telephone, personal digital assistant (PDA), a programmed microprocessor or microcontroller and peripheral integrated circuit element(s), and ASIC or other integrated circuit, a digital signal processor, a hard-wired electronic or logic circuit such as a discrete element circuit, a programmable logic device such as a PLD, PLA, FPGA, PAL, or the like. In general, any device capable of implementing the processes described herein can be used to implement the systems and techniques according to this invention.

It is to be appreciated that the various components of the technology can be located at distant portions of a distributed network and/or the Internet, or within a dedicated secure, unsecured and/or encrypted system. Thus, it should be appreciated that the components of the system can be combined into one or more devices or co-located on a particular node of a distributed network, such as a telecommunications network. As will be appreciated from the description, and for reasons of computational efficiency, the components of the system can be arranged at any location within a distributed network without affecting the operation of the system. Moreover, the components could be embedded in a dedicated machine.

Furthermore, it should be appreciated that the various links connecting the elements can be wired or wireless links, or any combination thereof, or any other known or later developed element(s) that is capable of supplying and/or communicating data to and from the connected elements. The term module as used herein can refer to any known or later developed hardware, software, firmware, or combination thereof that is capable of performing the functionality associated with that element. The terms determine, calculate and compute, and variations thereof, as used herein are used interchangeably and include any type of methodology, process, mathematical operation or technique.

Moreover, the disclosed methods may be readily implemented in software, e.g., as a computer program product having one or more modules each adapted for one or more functions of the software, executed on a programmed general purpose computer, cellular telephone, PDA, a special purpose computer, a microprocessor, or the like. In these instances, the systems and methods of this invention can be implemented as a program embedded on a personal computer such as a JAVA®, CGI or Perl script, as a resource residing on a server or graphics workstation, as a routine embedded in a dedicated image system, or the like. The systems and methods of this invention can also be implemented by physically incorporating this system and method into a software and/or hardware system, such as the hardware and software systems of a computer. Such computer program products and systems can be distributed and employ a client-server architecture.

The embodiments described above are intended to be exemplary. One skilled in the art recognizes that numerous alternative components and embodiments that may be substituted for the particular examples described herein and still fall within the scope of the invention.

We claim:

1. A process for modeling payment bundles using historical claims data comprising:
   importing, into at least a first modeler claims database, historical claims data for multiple types of claims;
   selecting, by payment bundling logic operating on at least one processor, at least one representative claim for payment bundle modeling, wherein the at least one representative claim is selected based on at least one of the following group consisting of type of medical procedure, provider specialty, provider name, patient condition and location of medical procedure;
   modifying, by the payment bundling logic, the data associated with the selected at least one representative claim to reflect a specific date range, wherein the specific data range includes therein a date for each medical procedure from the selected at least one representative claim;
   reviewing, by the payment bundling logic, the modified data associated with the selected at least one representative claim to identify at least one event therein to use to trigger a payment bundle;
   searching, by the payment bundling logic, the at least a first modeler claims database, to identify additional claims related to the representative claim, wherein a claim is related if it falls in the specific date range and meets one or more additional predetermined criteria;
   associating, by the payment bundling logic, the representative claim and identified related additional claims with the identified at least one event used to trigger a payment bundle; and
   determining, by the payment bundling logic, a modeled price for the payment bundle, wherein the modeled price includes a single payment for the combination of the representative claim and any identified related claims.

2. The process in accordance with claim 1, wherein the at least one event that triggers a payment bundle is identification by the payment bundling logic of a specific diagnosis related group (DRG) code in a claim.

3. The process in accordance with claim 1, further comprising:
   comparing, by the payment bundling logic, the modeled price for the payment bundle against the sum of individual payment amounts for each of the representative claims and identified related claims; and
   updating the payment bundle to exclude one or more of the identified related claims therefrom.

4. The process in accordance with claim 1, wherein the one or more additional predetermined criteria includes a same patient ID.

5. The process in accordance with claim 1, wherein the payment bundling logic further models distribution of the single payment in allowed amounts to one or more providers associated with the representative claim and identified related additional claims in the payment bundle.

6. The process in accordance with claim 5, wherein the payment bundling logic applies one or more rules that vary individual allowed amounts in accordance with one or more of an original fee-for-service amount under an applicable representative claim and identified related additional claims in the payment bundle, complications experienced by a patient associated with the representative claim and identified related additional claims in the payment bundle, and secondary diagnoses attributed to the patient associated with the representative claim and identified related additional claims in the payment bundle.

7. The process in accordance with claim 5, wherein the payment bundling logic applies one or more rules that vary individual allowed amounts in accordance with a defined role of one or more providers associated with the representative claim and identified related additional claims in the payment bundle.

8. A processor programmed with executable code for modeling payment bundles using historical claims data comprising:
   first payment bundling logic for selecting at least one representative claim for payment bundle modeling;
   second payment bundling logic for modifying data associated with the selected at least one representative claim to reflect a specific date range, wherein the specific data range includes therein a date for each medical procedure from the selected at least one representative claim;
   third payment bundling logic for analyzing the modified data associated with the selected at least one representative claim to identify at least one event therein to use to trigger a payment bundle;
   fourth payment bundling logic for searching at least a first modeler claims database, to identify additional claims related to the representative claim, wherein a claim is related if it falls in the specific date range and meets one or more additional predetermined criteria;
   fifth payment bundling logic for associating the representative claim and identified related additional claims with the identified at least one event used to trigger a payment bundle; and
   sixth payment bundling logic for determining a modeled price for the payment bundle, wherein the modeled price includes a single payment for the combination of the representative claim and any identified related claims.

9. The processor of claim 8, wherein the at least one representative claim is selected based on at least one of the following group consisting of type of medical procedure, provider specialty, provider name, patient condition and location of medical procedure.

10. The processor in accordance with claim 8, wherein the at least one event that triggers a payment bundle is identification by the payment bundling logic of a specific diagnosis related group (DRG) code in a claim.

11. The processor in accordance with claim 8, further comprising:
   seventh payment bundling logic for comparing the modeled price for the payment bundle against the sum of individual payment amounts for each of the representative claims and identified related claims and updating the payment bundle to exclude one or more of the identified related claims therefrom.

12. The processor in accordance with claim 8, wherein the one or more additional predetermined criteria includes a same patient ID.

13. The processor in accordance with claim 8, comprising seventh payment bundling logic for modeling distribution of the single payment in allowed amounts to one or more providers associated with the representative claim and identified related additional claims in the payment bundle.

14. The processor in accordance with claim 13, wherein the eighth payment bundling logic applies one or more rules that vary individual allowed amounts in accordance with one or more of an original fee-for-service amount under an applicable representative claim and identified related additional claims in the payment bundle, complications experienced by a patient associated with the representative claim and identified related additional claims in the payment bundle, and secondary diagnoses attributed to the patient associated with the representative claim and identified related additional claims in the payment bundle.

15. The processor in accordance with claim 13, wherein the eighth payment bundling logic applies one or more rules that vary individual allowed amounts in accordance with a defined role of one or more providers associated with the representative claim and identified related additional claims in the payment bundle.

* * * * *